United States Patent
Coffey et al.

(10) Patent No.: US 11,151,222 B1
(45) Date of Patent: Oct. 19, 2021

(54) SKY EXPOSURE AND SOLAR RADIATION FOR FORMS OF LIFE

(71) Applicant: STWRD, Inc., New York, NY (US)

(72) Inventors: Brendan Michael Coffey, Westport, CT (US); Alexi Surtees Coffey, Westport, CT (US)

(*) Notice: Subject to any disclaimer, the term of this patent is extended or adjusted under 35 U.S.C. 154(b) by 266 days.

(21) Appl. No.: 16/408,050

(22) Filed: May 9, 2019

Related U.S. Application Data

(60) Provisional application No. 62/669,217, filed on May 9, 2018.

(51) Int. Cl.
| | |
|---|---|
| *G06F 17/18* | (2006.01) |
| *G01J 1/42* | (2006.01) |
| *G01W 1/12* | (2006.01) |

(52) U.S. Cl.
CPC .............. *G06F 17/18* (2013.01); *G01J 1/42* (2013.01); *G01W 1/12* (2013.01); *G01J 2001/4266* (2013.01)

(58) Field of Classification Search
CPC ... G06F 17/18; G01W 1/12; G01J 1/42; G01J 2001/4266
See application file for complete search history.

(56) References Cited

FOREIGN PATENT DOCUMENTS

| | | | | | |
|---|---|---|---|---|---|
| BR | 112014015313 B1 | * | 4/2021 | ............. | A61F 9/02 |
| CN | 103090868 B | * | 1/2016 | ............. | G01C 21/20 |
| CN | 109416413 | * | 3/2019 | ............. | H02S 10/00 |
| EP | 3455657 | * | 3/2019 | ............. | H02S 10/00 |
| IN | 1663/DEL/2012 A | * | 12/2014 | ............. | G06Q 1/00 |
| KR | 2014-0021179 A | * | 2/2014 | ............. | G06F 17/30 |
| KR | 1807579 | * | 12/2017 | ............. | G06F 17/00 |

OTHER PUBLICATIONS

Josep Calbo, a Method for Sky-Condition Classification from Ground-Based Solar Radiation Measurements, Dec. 2001, 7 pages (Year: 2001).*

Khalil Benmouiza, Classification of hourly solar radiation using fuzzy c-means algorithm for optimal stand-alone PV system sizing, Mar. 25, 2016, 9 pages (Year: 2016).*

* cited by examiner

*Primary Examiner* — Tung S Lau

(57) ABSTRACT

Methodologies related to sky exposure and solar radiation for forms of life are presented, including sky exposure, solar radiation, forms of life potential, forms of life care, solar calibration, recommendations for associated products and services, greenprints, and related concepts. These may be achieved in part by capturing sky exposure data, evaluating sky exposure data, classifying sky exposure data, assessing solar radiation values, evaluating forms of life, and classifying form of life suitability.

20 Claims, 22 Drawing Sheets

FIG. 10A

|  | 1030<br>Growth Conditions<br>1 (lbs) | | 1040<br>Growth Conditions<br>2 (lbs) | | 1050<br>Growth Conditions<br>3 (lbs) | |
|---|---|---|---|---|---|---|
| 1010<br>French<br>Radishes | 80 | 1013 | 150 | 1014 | 20 | 1015 |
| 1020<br>Runner Beans | 60 | 1023 | 200 | 1024 | 70 | 1025 |

FIG. 10B

|  | 1030b<br>Growth Conditions<br>1 (lbs) CO2<br>Sequestered | | 1040b<br>Growth Conditions<br>2 (lbs) CO2<br>Sequestered | |
|---|---|---|---|---|
| 1010b<br>Sugar Maple Tree | 25 | 1013b | 10 | 1014b |
| 1020b<br>Redwood Tree | 5 | 1023b | 40 | 1024b |
| 1030b<br>Douglas Fir | 15 | 1033b | 18 | 1034b |

SKY EXPOSURE AND SOLAR RADIATION FOR FORMS OF LIFE

CROSS-REFERENCE TO RELATED APPLICATIONS

This application claims the benefit of U.S. Provisional Application No. 62/669,217, filed May 9, 2018. The contents of the above-identified application are incorporated by reference in their entirety as if recited in full herein.

BACKGROUND OF THE INVENTION

Field of Invention

The inventions disclosed herein generally relate to sky exposure and solar radiation for forms of life. More specifically, inventions disclosed herein relate to sky exposure, solar radiation, forms of life potential, forms of life care, solar calibration, recommendations for associated products and services, greenprints, and related concepts and methodologies.

Description of Related Art

Related art may include applications that use augmented reality, location information (e.g. from GPS), and orientation information of a mobile device, to inform a user. An example of such an application is early versions of the Sky Walk app, by Vito Technology, Inc. of Alexandria, Va., which uses augmented reality to educate a user on the night sky, including stars, planets, etc. Other related art may include hardware devices that can be used to track the sun's movements. Additional related art may include drones that are used to plant seeds.

BRIEF SUMMARY OF EMBODIMENTS OF THE INVENTION

In accordance with one or more embodiments of the inventions, methods and systems related to sky exposure and solar radiation for forms of life are disclosed. Certain of the systems and methods include the steps of: capturing sky exposure data in a location along at least some part of one or more solar paths between a winter solstice solar path and a summer solstice solar path using one or more data collection sensors; evaluating captured sky exposure data using one or more computer-based tools; classifying portions of the captured sky exposure data as indicative of at least one of sky and sky blockages; assessing one or more solar radiation values received by at least some of the location during at least an instant in time, based at least in part on the captured sky exposure data; evaluating one or more forms of life based at least in part on one or more of the assessed solar radiation values; and classifying form of life suitability based at least in part on the evaluation of one or more forms of life and also based at least in part on one or more of the assessed solar radiation values.

Certain of the methods may include one or more of: presenting to a user one or more of the solar paths at the location and instructing the user to orient one or more data collection sensors to capture additional solar radiation values at the location; estimating insurance-related parameters relating to one or more of the forms of life; incorporating additional data, including at least some conditions data, in the evaluation of one or more forms of life and in the classification of form of life suitability; recommending a customized care plan for at least one of the one or more forms of life based at least in part on one or more of the assessed solar radiation values; mapping data from at least one of the one or more solar radiation values into a model based at least in part on the classification of form of life suitability; implementing at least a portion of the model via remote operation; capturing additional sky exposure data along at least some additional part of the one or more solar paths between the winter solstice solar path and the summer solstice solar path, at least in the form of image data and assessing additional portions of at least one of the one or more solar paths using the captured additional sky exposure image data, using one or more computer-based systems; improving performance of at least one of evaluating one or more forms of life and classifying form of life suitability by utilizing additional data from disparate locations; presenting to the user one or more recommendations based at least in part on one or more of the evaluation of one or more forms of life, the classification of form of life suitability, and one or more of the solar radiation values; quantifying a productivity value of at least one of the forms of life, based at least in part on one or more of the solar radiation values; providing medium enhancing recommendations to the user based at least in part on the evaluation of one or more forms of life, the classification of form of life suitability, and conditions data; assessing health status of one or more of the forms of life and providing one or more health solutions recommendations to the user, based at least in part on the assessed health status of the one or more forms of life; appraising one or more of the forms of life using computer-based systems; providing training recommendations to improve forms of life caring skills; providing one or more structural modification recommendations for the location based at least in part on the evaluation of one or more forms of life and based at least in part on conditions data; enabling at least one of the purchase and sale of at least one of a form of life and a recommendation; and assessing human wellness factors related to one or more of the evaluation of forms of life and one or more of the solar radiation values.

Certain of the embodiments may include a system to evaluate one or more forms of life and classify form of life suitability for a location by assessing one or more solar radiation values in the location for a period of time, the system comprising: one or more data collection sensors for capturing sky exposure data in a location along at least some part of one or more solar paths between a winter solstice solar path and a summer solstice solar path; one or more computer-based tools for evaluating captured sky exposure data; control logic for classifying portions of the captured sky exposure data as indicative of at least one of sky and sky blockages; control logic for assessing one or more solar radiation values received by at least some of the location during at least an instant in time, based at least in part on the captured sky exposure data; control logic for evaluating one or more forms of life based at least in part on one or more of the assessed solar radiation values; and control logic for classifying form of life suitability based at least in part on the evaluation of one or more forms of life and also based at least in part on one or more of the assessed solar radiation values.

Certain of the embodiments may include a non-transitory computer readable medium storing instructions that when executed by one or more processors cause the one or more processors to: capture sky exposure data in a location along at least some part of one or more solar paths between a winter solstice solar path and a summer solstice solar path using one or more data collection sensors; evaluate captured sky exposure data using one or more computer-based tools; classify portions of the captured sky exposure data as indicative of at least one of sky and sky blockages; assess one or more solar radiation values received by at least some of the location during at least an instant in time, based at least in part on the captured sky exposure data; evaluate one or more forms of life based at least in part on one or more of the assessed solar radiation values; and classify form of life suitability based at least in part on the evaluation of one or more forms of life and also based at least in part on one or more of the assessed solar radiation values.

BRIEF DESCRIPTION OF THE DRAWINGS

For a more complete understanding of various embodiments of the present invention, reference is now made to the following descriptions taken in connection with the accompanying drawings in which:

FIG. 10A illustrates a table comparing productivity values of three forms of life with different solar radiation values.

FIG. 10B illustrates a table comparing productivity values of two forms of life with different growth conditions.

DETAILED DESCRIPTION OF THE PREFERRED EMBODIMENTS

Figure 1A:
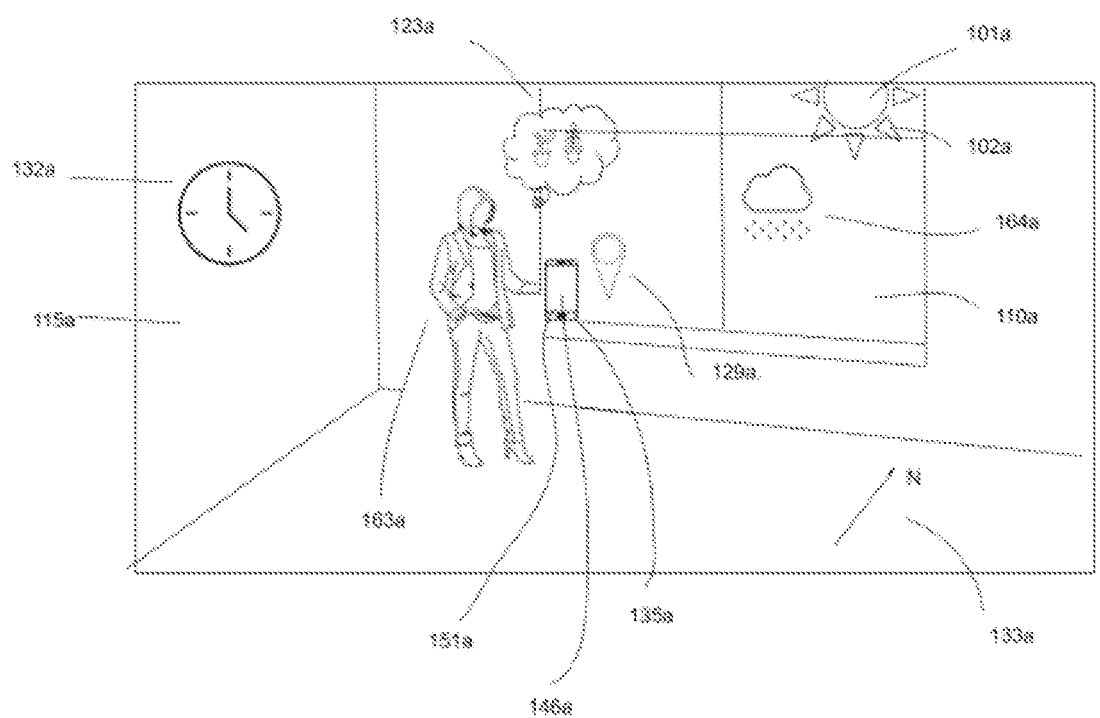
FIG. 1A illustrates a user capturing solar exposure data for forms of life suitability.

FIG. 1A illustrates a user capturing solar exposure data for forms of life suitability. User 163 is illustrated holding data collection sensor 135 at a location 129, evaluating one or more growing conditions data, such as one or more solar radiation values 102 by assessing sky exposure data 110 and additional data, including weather 164, to classify forms of life suitability 123. FIG. 1 illustrates an indoor setting, including walls 115 and our sun 101 is illustrated through the window. Data collection sensor 135 may be oriented around to capture additional solar radiation values 102, such as the circle method or solar calibration, and incorporating additional data such as direction 133 or user preferences. Forms of life suitability 123 may be presented to user 163. Recommendations 151 may also be presented.

Figure 1B:
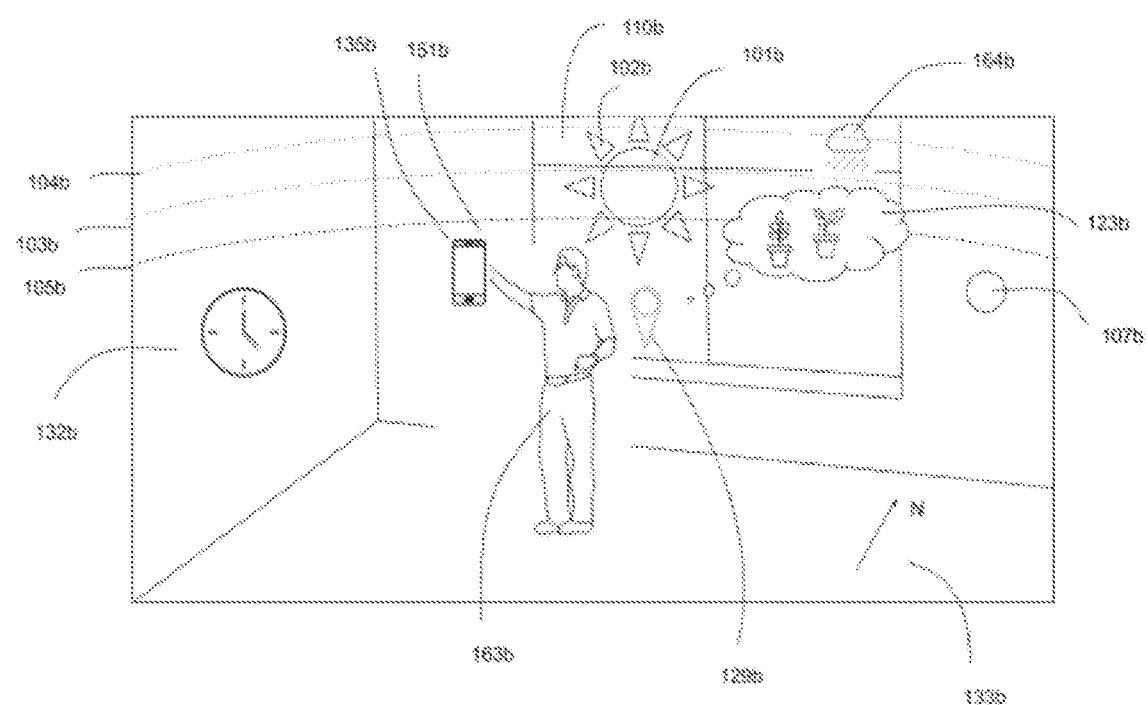
FIG. 1B illustrates a user capturing solar exposure data for forms of life suitability, showing multiple arcs representative of solar paths.

FIG. 1B illustrates a user capturing solar exposure data for forms of life suitability, showing multiple arcs representative of solar paths. User 163b holds data sensor collector 135b in location 129b, evaluating one or more solar path, such as summer solstice solar path 104b, winter solstice solar path 105b, or solar path 103b, and also other growing conditions data, such as additional solar radiation values 102b by assessing sky exposure 110b to classify form of life suitability 123b. Data collection sensor 135b may be moved around or oriented to capture additional sky exposure data and incorporate additional data such as direction 133b or user preferences. Forms of life suitability 123b may be presented to user 163b. Customized care recommendations 151b or other recommendations may be provided. Also illustrated are the sun 101b and weather 164b.

Figure 1C:
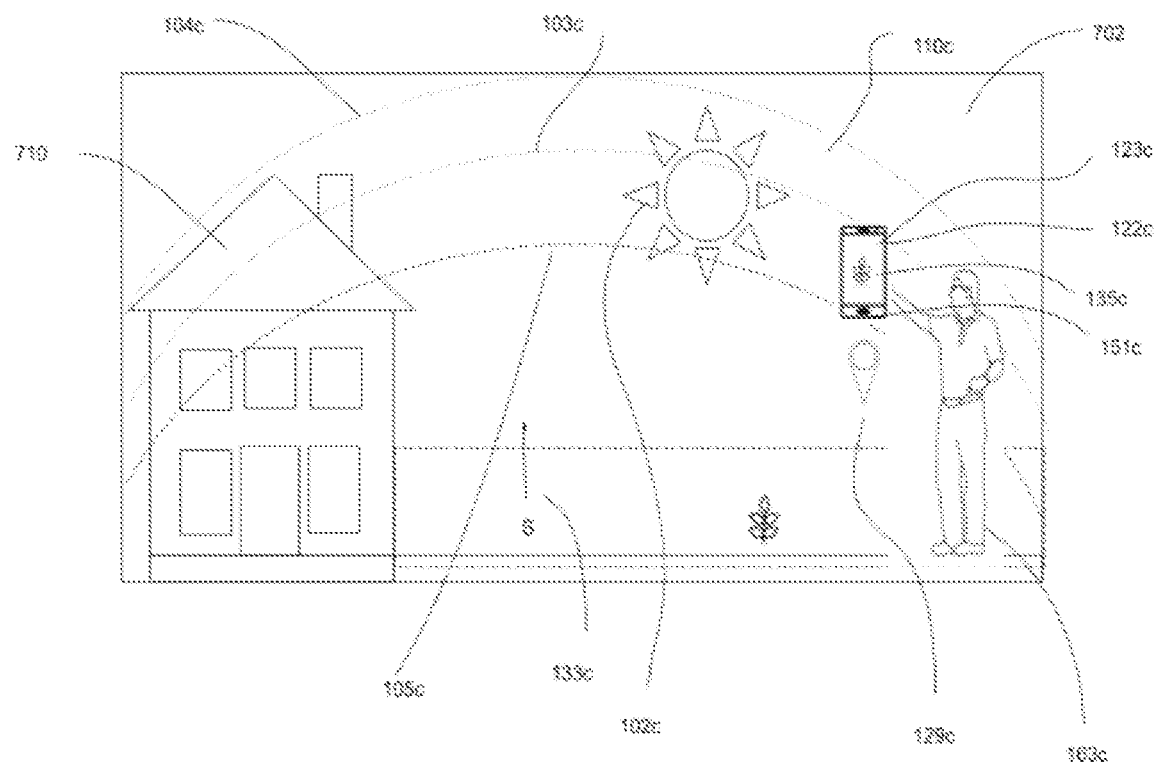
FIG. 1C illustrates form of life suitability based on solar radiation values and other data.

FIG. 1C illustrates form of life suitability based on solar radiation values and other data. User 163c is illustrated evaluating forms of life 122c. User 163c holds data collection sensor 135c at location 129c, evaluating one or more solar path, such as summer solstice solar path 104c, winter solstice solar path 105c, or solar path 103c and other conditions data, such as additional solar radiation values 102c by assessing sky exposure 110c to classify form of life suitability 123c. Data collection sensor 135c may be moved around or oriented to capture additional sky exposure data and incorporate additional data such as direction 133c or user preferences 131c. Forms of life suitability 123c may be presented to the user. Customized recommendations 151c may also be presented.

Figure 2:
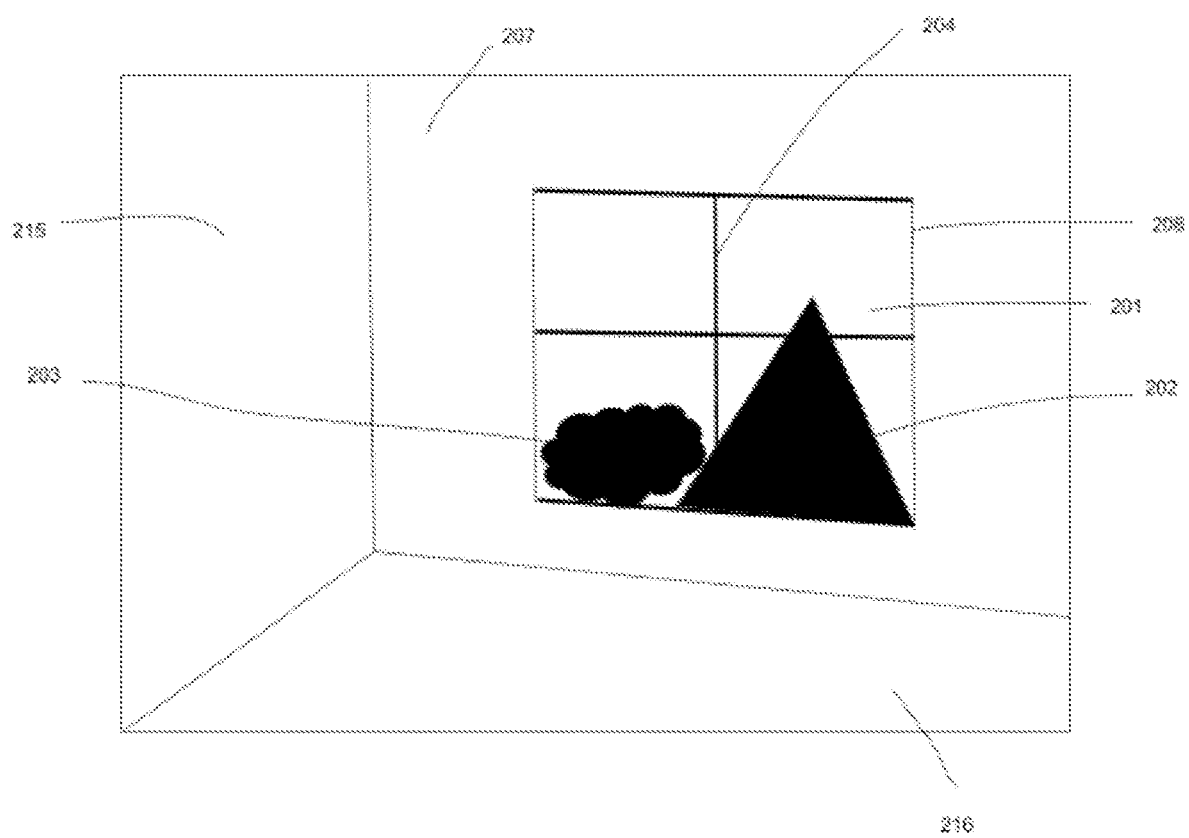
FIG. 2 illustrates available sky exposure and blockages.

FIG. 2 illustrates available sky exposure and blockages. Illustrated in FIG. 2 is an indoor location, with walls 215 that are also sky blockage and floor 216 that is also sky blockage. Window 208 is illustrated, as is window frame 204 which is also sky blockage. Sky exposure data is derived from sky 201 seen through window 208. Computer-based tools, including segmentation methods, classify portions of sky 201; and they also classify portions of sky blockage including mountain 202, tree 203, window frame 204, floor 216, wall 215. Captured sky exposure data values are evaluated.

Figure 3:
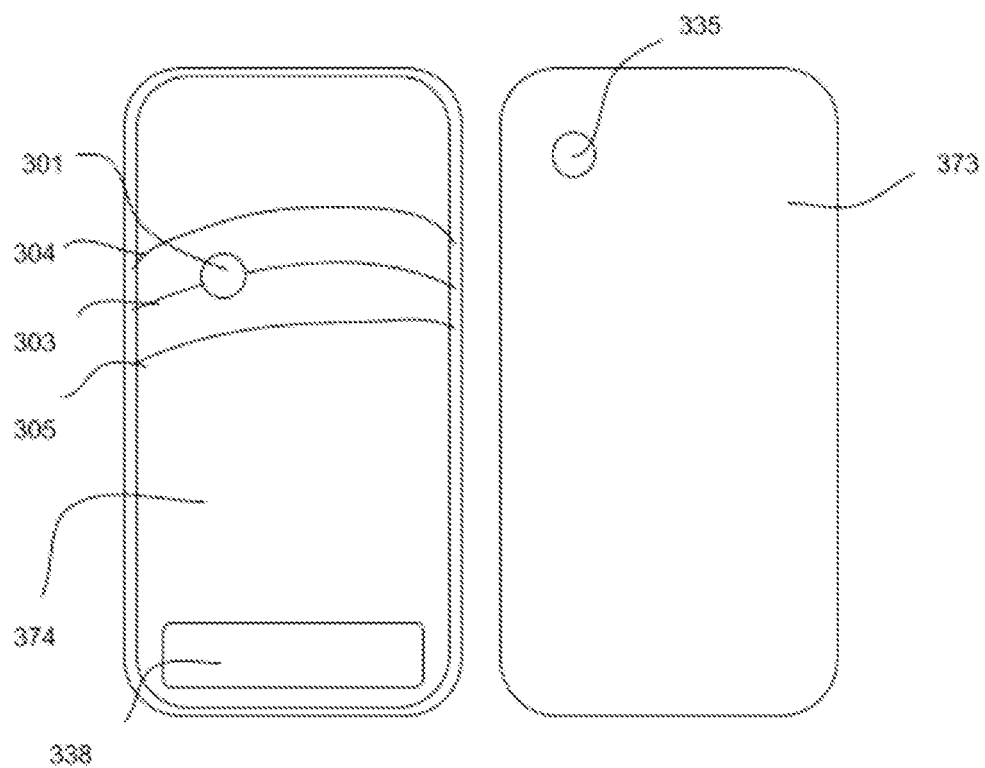
FIG. 3 illustrates an example of presenting to a user one or more solar paths.

FIG. 3 illustrates an example of presenting to a user one or more solar paths. Mobile communication device 373 is illustrated, which may be a mobile phone, a tablet, or many other kinds of mobile communication devices. As illustrated, mobile communications device 373 includes data collection sensor 335. Display 374 is illustrated, and may include instructions 338, which may instruct the user to orient data collection sensor 335 to capture additional portions of solar path 303, and thus to capture additional sky exposure data. Display 374 is illustrated presenting to a user one or more solar paths, such as winter solstice solar path 305, solar path 303, and summer solstice solar path 304. Display 374 also illustrates sun 301 along solar path 303.

Figure 4:
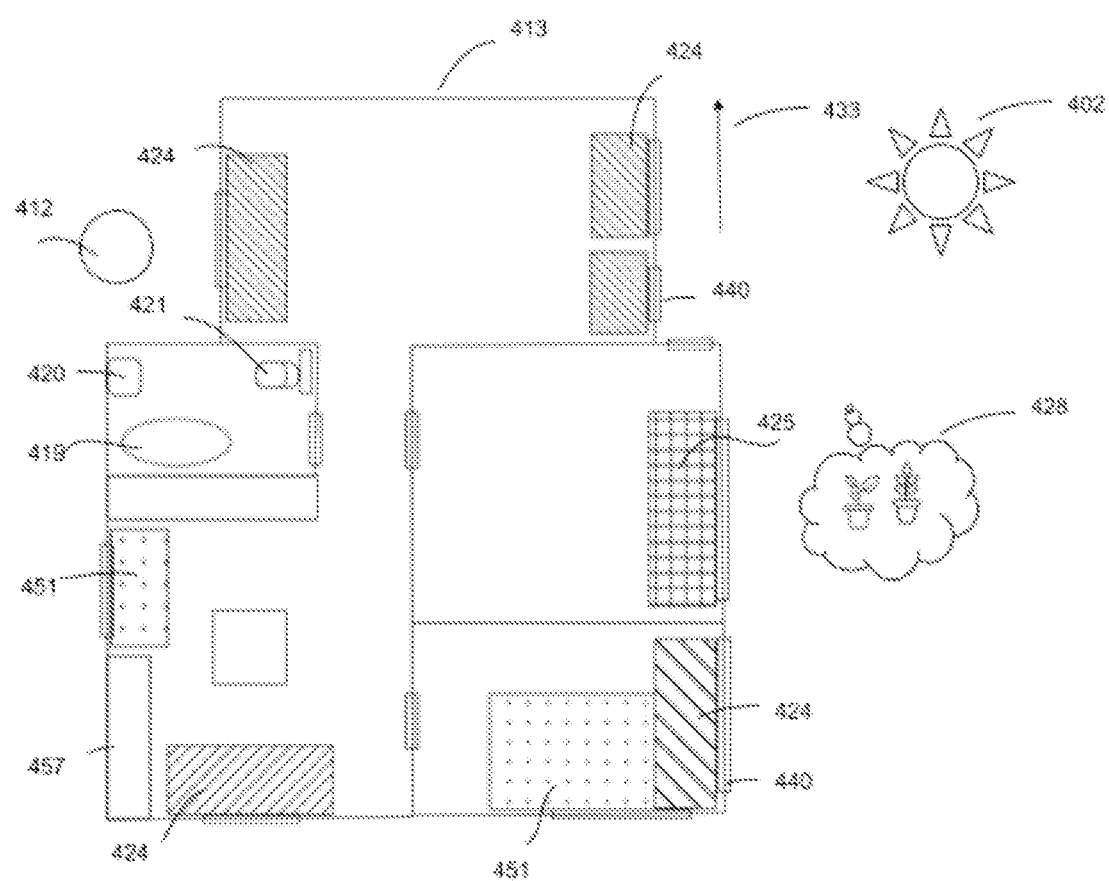
FIG. 4 illustrates an example of a model of mapped data.

FIG. 4 illustrates an example of a model of mapped data. Building 413 is illustrated, including rooms with bath 419, sink 420, and toilet 421. Multiple zones are illustrated, including Zone 1 424, Zone 2 425, and Zone 3 426. Each zone 424, 425, and 426 receives different solar radiation values 402. Data is mapped from at least some of solar radiation values 402 into a model based at least in part on the classification of form of life suitability. A model may categorize forms of life suitability in zones such as 424 or 425, and may include additional data such as user preferences, direction 433, or other image data. Image data may include, for example, image data relating to opening 440, which may be a door or a window, for example. The system may provide recommendations, for example structural modifications 457 or enhancing mediums. A model may be predictive such as anticipating the effects of one or more trees 412 over a period of time. As illustrated, recommendations may be provided for a particular area 451, or other areas.

Figure 5:
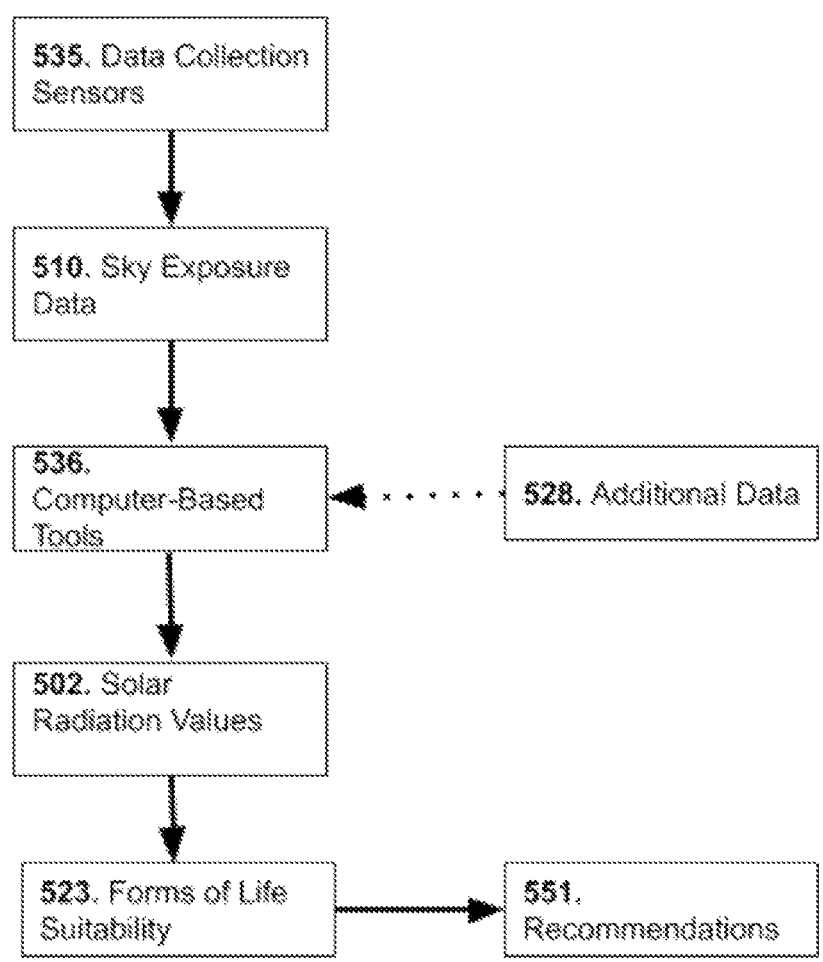
FIG. 5 illustrates an exemplary data.

FIG. 5 illustrates an exemplary data flow. One or more data collection sensors 535 may capture sky exposure data 510 and one or more solar radiation values 502, through sky exposure and detection and may combine additional data 528. Some exemplary forms of additional data may include weather, soil quality, time of day, user preferences, temperature data, humidity data, air pollution data, USDA Hardiness Zone, spatial parameters, and many other forms of additional data. One or more computer-based tools 536 may evaluate forms of life suitability. Recommendations 551 may also be presented, for example, artificial lighting or specific fertilizer related to one or more forms of life or solar radiation values, and also potentially health solutions or customized care plan recommendations, or other recommendations. Additional data 528 may be included at any step or point in the process. A specific form of life, for example a *Monstera deliciosa*, may be selected in advance of capturing the solar radiation value and evaluated for suitability accordingly 523. A specific form of life may similarly be selected at any point in the process, and may be included, along with care and many other suggestions, recommendations by the system.

Figure 6:
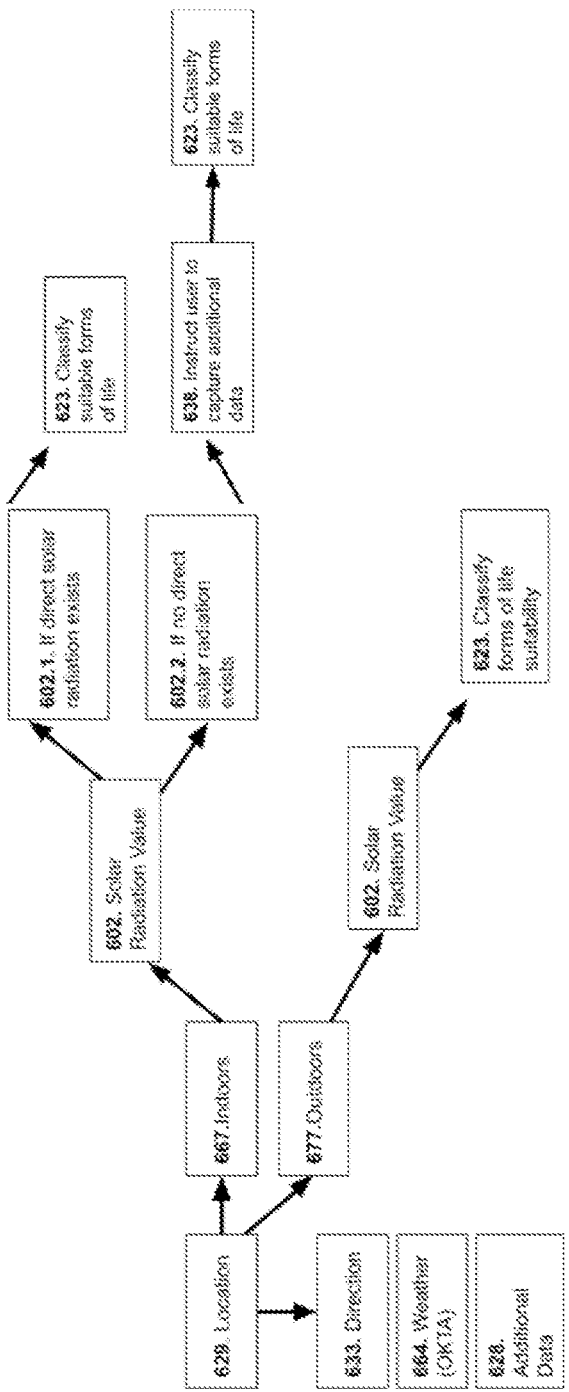
FIG. 6 illustrates user instructions based in part on location changes.

FIG. 6 illustrates user instructions based in part on location changes. As illustrated, and depending on a location 629, and other data such as direction 633, weather 664, and additional data 628. Weather 664 may, for example, be pulled via satellite weather API (application program interface), and may also come from real-time weather or solar calibration capture. Additional data 628 may include, for example, time of day, time of year, or any other type of additional data. User instructions may vary, such as if the data collection sensor is collecting data indoors 667 or outdoors 677, and the user may be presented with different instructions in different cases. By way of example, in some instances, a user will see the classification for forms of life suitability 623 directly after capturing solar radiation values 602, in other instances the user may be guided to add in or orient or otherwise move a data collection sensor to capture additional data 638 before classifying forms of life suitability 623. As illustrated, a user who is outdoors 677 with one or more data collection sensors may capture one or more solar radiation values 602, after which the system may classify forms of life suitability 623. A user who is indoors 667 with one or more data collection sensors, may capture one or more solar radiation values 602, after which they system may determine if direct solar radiation exists 602.1 in the location, or if no direct solar radiation exists 602.2 in the location. If direct solar radiation exists 602.1 at the location, the system may classify suitable forms of life 623. If no direct solar radiation exists 602.2 at the location, the system may instruct user to capture additional data 638, and thereafter classify suitable forms of life 623.

Figure 7A:
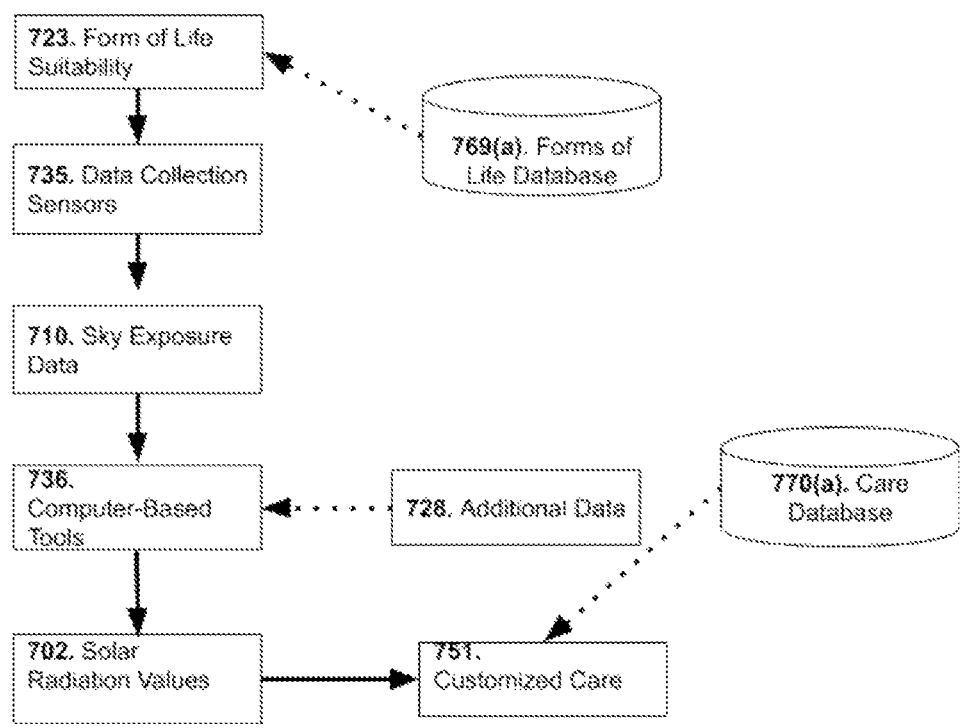
FIG. 7A illustrates a customized care plan flow according to some embodiments.

FIG. 7A illustrates a customized care plan flow according to some embodiments. A customized care plan may consider several different types of data, such as a form of life and solar radiation values 702. Forms of life database 769(*a*), care database 770(*a*) and additional data 728 may be utilized. Additional data 728 may include, by way of nonlimiting example, user preferences, for instance, level of commitment, expertise, or other forms of life in care plan. Computer-based tools 736(*a*) may be used to evaluate, and present a customized care plan 771(*a*) and may include one or more care activities, for example, watering, fertilizing, propagating, repotting. Additional data 728 may be episodically included, and a customized care plan may be responsive to changes in weather or temperature, or user-generated inputs such as soil moisture analysis. As illustrated in FIG. 7(*a*), a customized care recommendation 751 may result from form of life suitability 723, data collected from data collection sensors 735, sky exposure data 710, computer-based tools 736, and solar radiation values 702. Care database 770(*a*) may also be utilized.

Figure 7B:
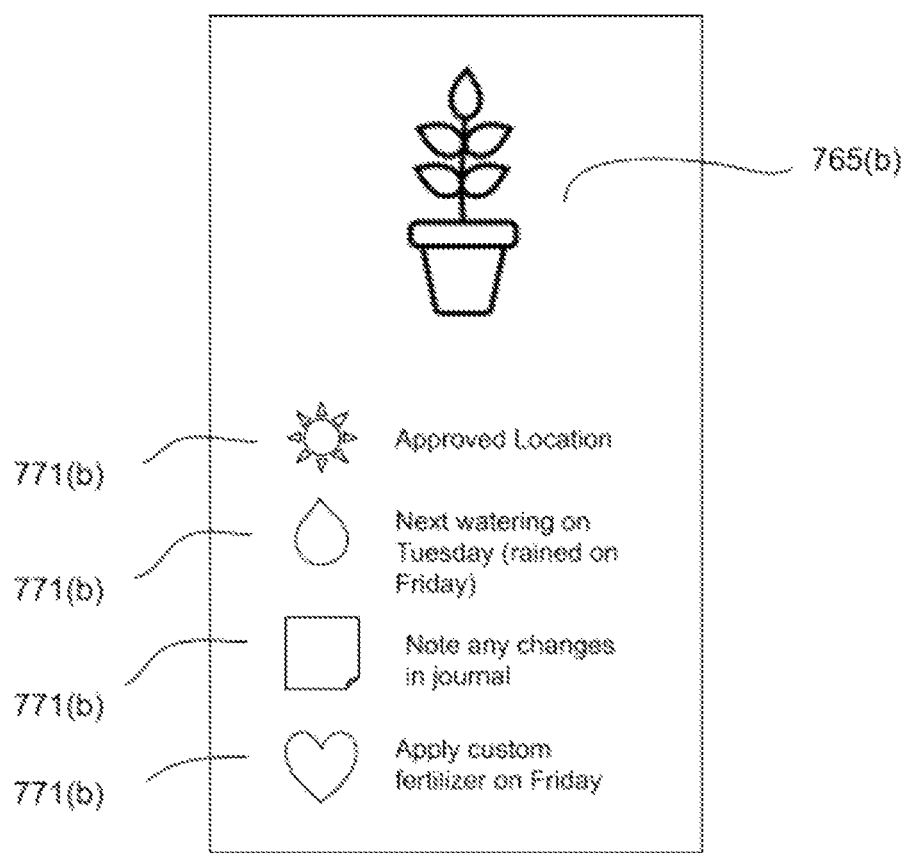
FIG. 7B illustrates presentation of a custom care plan for a form of life.

FIG. 7B illustrates presentation of a custom care plan for a form of life. Custom care plan 771(*b*) may take many forms, for example, presented via one or more user interfaces, and may include one or more forms of life 765(*b*). Some of all of customized care plan 771(*b*) may be responsive to additional data. For example, a watering schedule may be responsive to rain near a location, adjusting the watering to account for the additional precipitation, or temperature being used for the system to alert a user to move plant 765(*b*) in from a window to protect plant 765(*b*) from cold damage. Recommendations may vary depending on where the plant is located, and many other factors. Classifying form of life suitability for a saved location may be saved in the profile. As illustrated, customized care plan 771(*b*) may include one or more approved locations, a recommended schedule for care items such as watering, journal notes of changes, and a plan to apply a growing aid, such as fertilizer, at one or more designated times.

Figure 8:
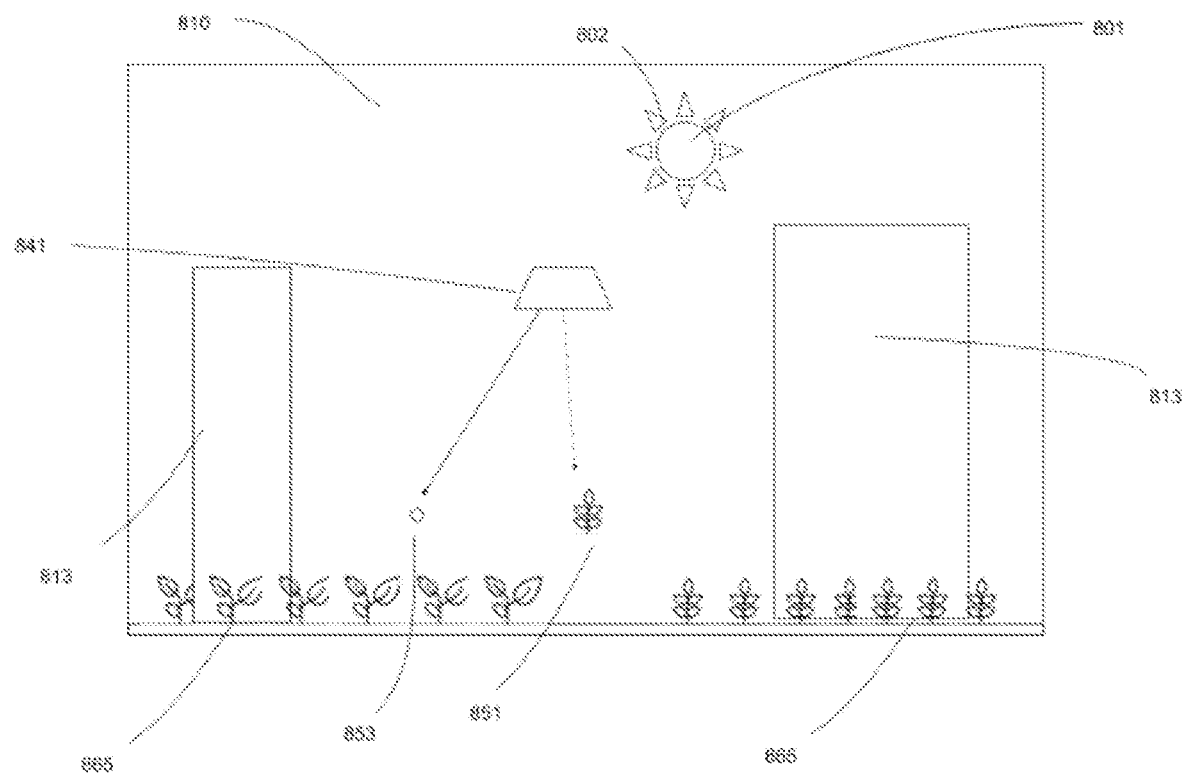
FIG. 8 illustrates an outdoor implementation of recommendations via drone.

FIG. 8 illustrates an outdoor implementation of recommendations via drone. As illustrated here by a drone, remote operation 841 may implement recommendations 851, such as medium enhancing recommendations 853 to forms of life 865. The system may consider solar radiation values 802 and sky exposure data 810, as well as blockagages such as from buildings 813. Our sun 801 is also illustrated.

Figure 9:
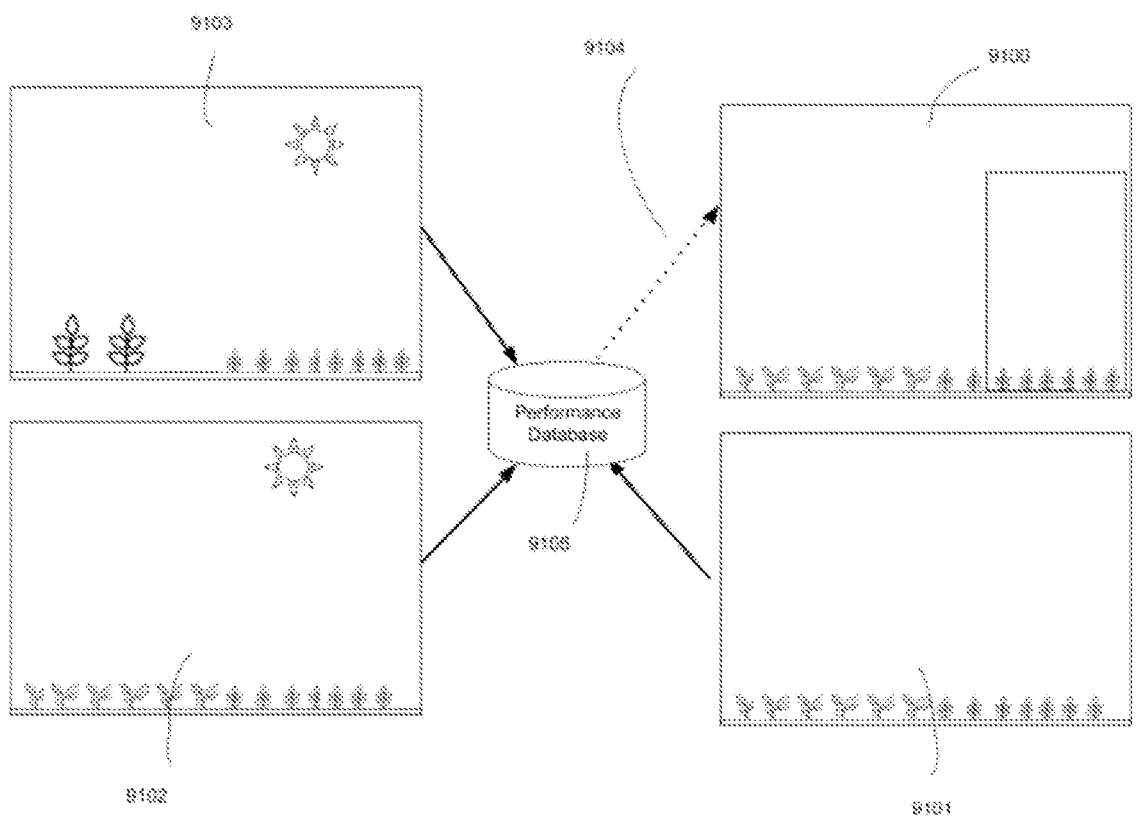
FIG. 9 illustrates utilizing additional disparate data to improve system performance.

FIG. 9 illustrates utilizing additional disparate data to improve system performance. Performance database 9105 is illustrated, which may utilize additional data 9104 from disparate locations 9101, 9102, 9103 to improve performance of one or more of classifications of forms of life suitability, sky detection evaluation, solar radiation values evaluation, and recommendations 9100.

FIG. 10A illustrates a table comparing productivity values of two forms of life with different solar radiation values. Two forms of life 1010, 1020 are listed in the table. Productivity values 1013, 1014, 1015, 1023, 1024, 1025 such as yield (lbs) may be quantified based at least in part on conditions data 1030, 1040, 1050. For example, a first soil mix may with conditions data 1 1030 may receive five hours of sun, while a second soil mix with conditions data 2 1040 may receive 9 hours of direct sun, while a third soil mix with conditions data 3 1050 may receive 2 hours of direct sun.

FIG. 10B illustrates a table comparing productivity values of three forms of life with different growth conditions. Three forms of life 1010*b*, 1020*b*, 1030*b* are listed in the table. Productivity values 1013*b*, 1014*b*, 1023*b*, 1024*b*, 1033*b*,

1034*b* such as CO2 sequestration (lbs) may be quantified based at least in part on growth conditions data 1030*b*, 1040*b*.

Figure 11:
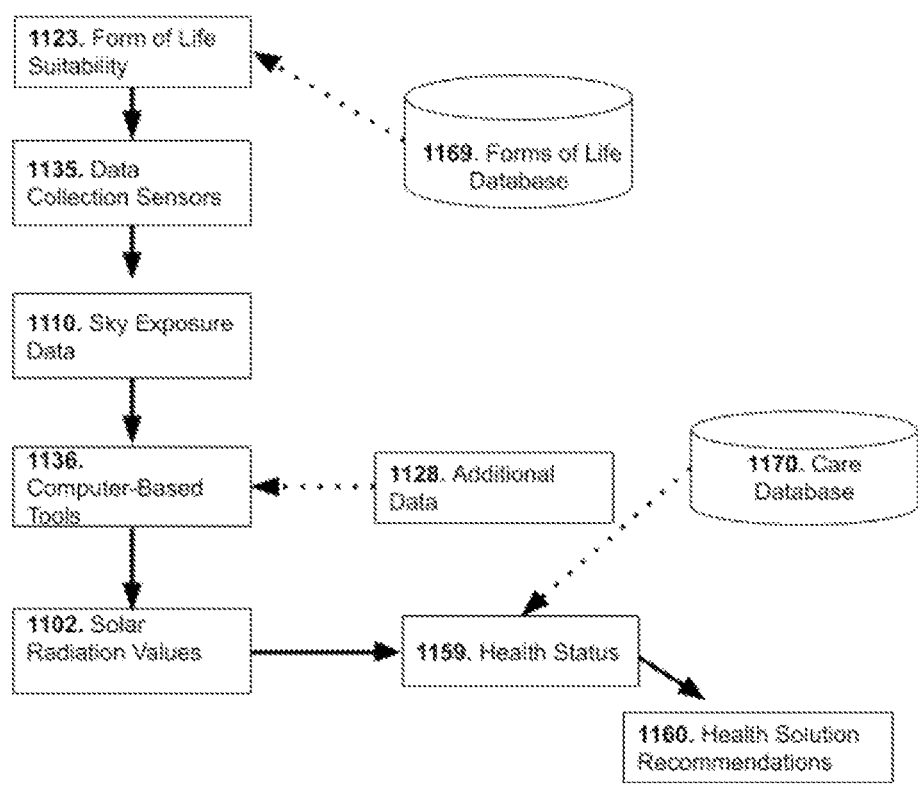
FIG. 11 illustrates an exemplary flow for health status and health solutions recommendations for forms of life.

FIG. 11 illustrates an exemplary flow for health status and health solutions recommendations for forms of life. Form of life health status 1159 may be assessed by evaluating form of life suitability 1123, sky exposure data 1110, and solar radiation values 1102 with data collected by data collection sensors 1135 and processed using computer-based tools 1136. Additional data 1128 may be utilized, such as image data, which may show a yellowing leaf for a particular plant, or user-generated data showing a case of tree blithe near a location. One or more health solutions recommendations 1160 may be provided based on the assessed health status. Forms of life database 1169 and care database 1170 may also be utilized.

Figure 12:
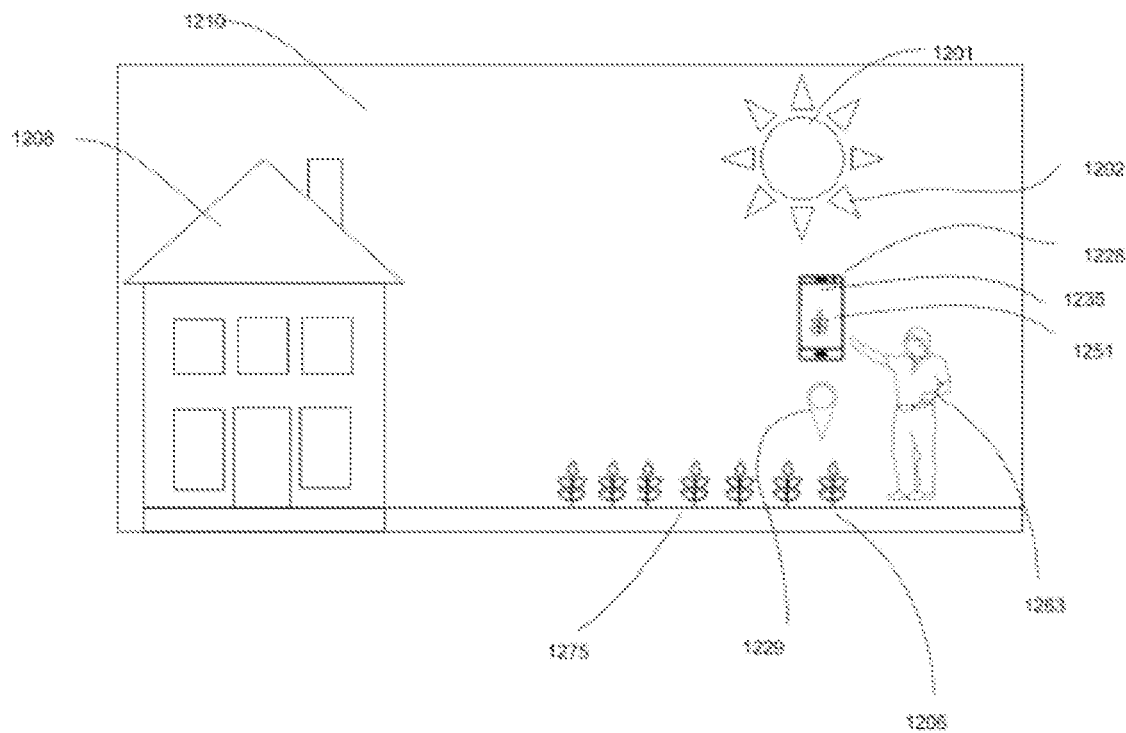
FIG. 12 illustrates providing training recommendations for forms of life caring skills.

FIG. 12 illustrates providing training recommendations for forms of life caring skills. One or more data sensor collectors 1235 may be used to collect data about a location. User 1263 may be presented with training recommendations 1251 to improve form of life caring skills 1275. Training recommendations 1251 may consider sky exposure data 1210, solar radiation values 1202 from sun 1201 and may also consider additional data 1228, for example, about user 1263 or location 1229.

Figure 13A:
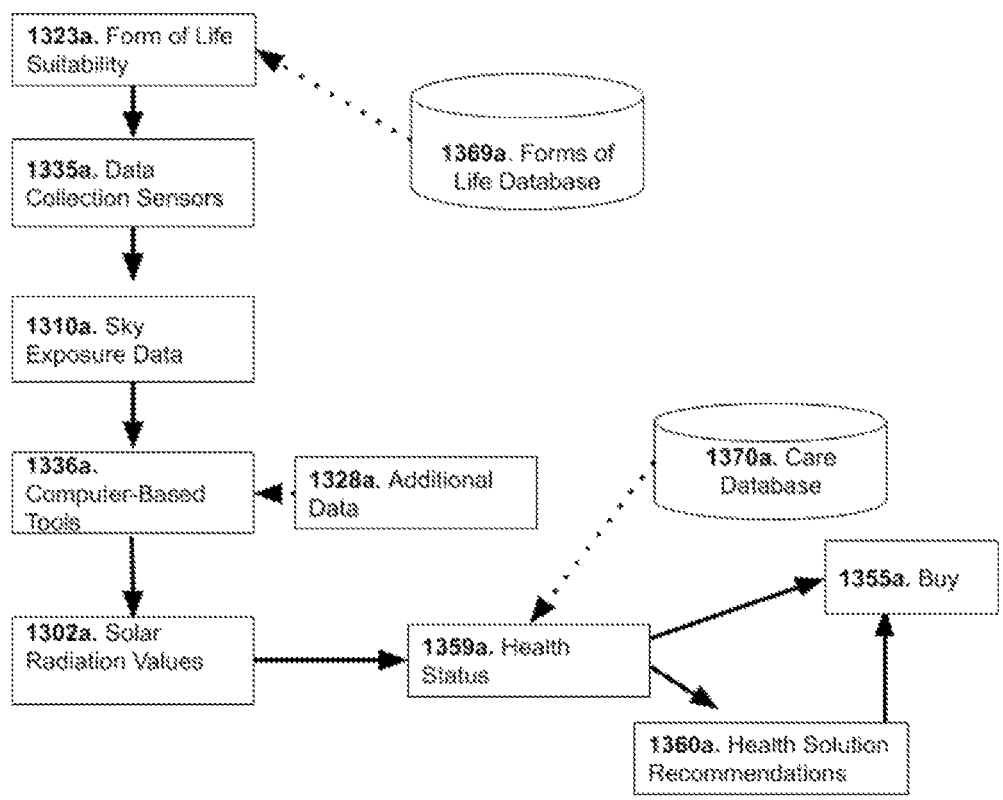
FIG. 13A illustrates an exemplary data flow for buying health solution recommendations.

FIG. 13A illustrates an exemplary data flow for buying health solution recommendations. A user may buy 1355*a* one or more health status assessments 1359*a* or one or more health solution recommendations 1360*a*. Such purchases may be presented (e.g. to a user) after data collection sensors 1335*a* and computer-based tools 1336*a* have been used to evaluate sky exposure data 1310*a* and assess solar radiation values 1302*a* and forms of life suitability 1323*a* for a location, or before. Additional data 1328*a*, such as user preferences, e-commerce or marketplace availability, or other conditions data may or may not also be evaluated. A purchase may be a one-time transaction or may be a subscription. It may occur in an app, e-commerce marketplace, virtual reality, augmented reality or any other mode or method of transaction. Forms of life database 1369*a* and care database 1370*a* may also be utilized in this process.

Figure 13B:
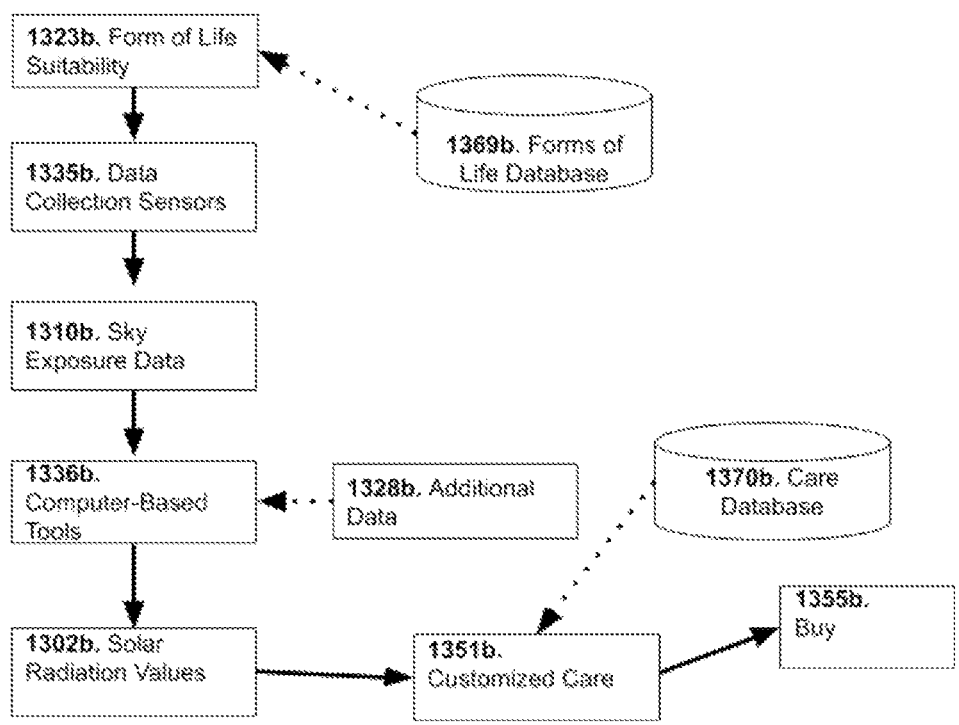
FIG. 13B illustrates an exemplary data flow for buying a customized care plan.

FIG. 13B illustrates an exemplary data flow for buying a customized care plan. One or more portions of Customized Care Plan 1351*b* for Form of Life Suitability 1323*b* may be purchased or bought 1355*b*, and may be presented (to a user) after data collection sensors 1335*b* and computer-based tools 1336*b* have been used to evaluate sky exposure data 1310*b* and assess solar radiation values 1302*b* and forms of life suitability 1323*b* for a location, or before. Additional data 1328*b*, such as user preferences, number of forms of life within plan, e-commerce or marketplace availability, or other conditions data may or may not also be evaluated. A purchase may be a one-time transaction or may be a subscription. It may occur in an app, e-commerce marketplace, virtual reality, augmented reality or any other mode or method of transaction, and may be presented (to a user) before or after a after a modified care plan analysis has taken place. Forms of life database 1369*b* and care database 1370*b* may also be utilized in this process.

Figure 13C:
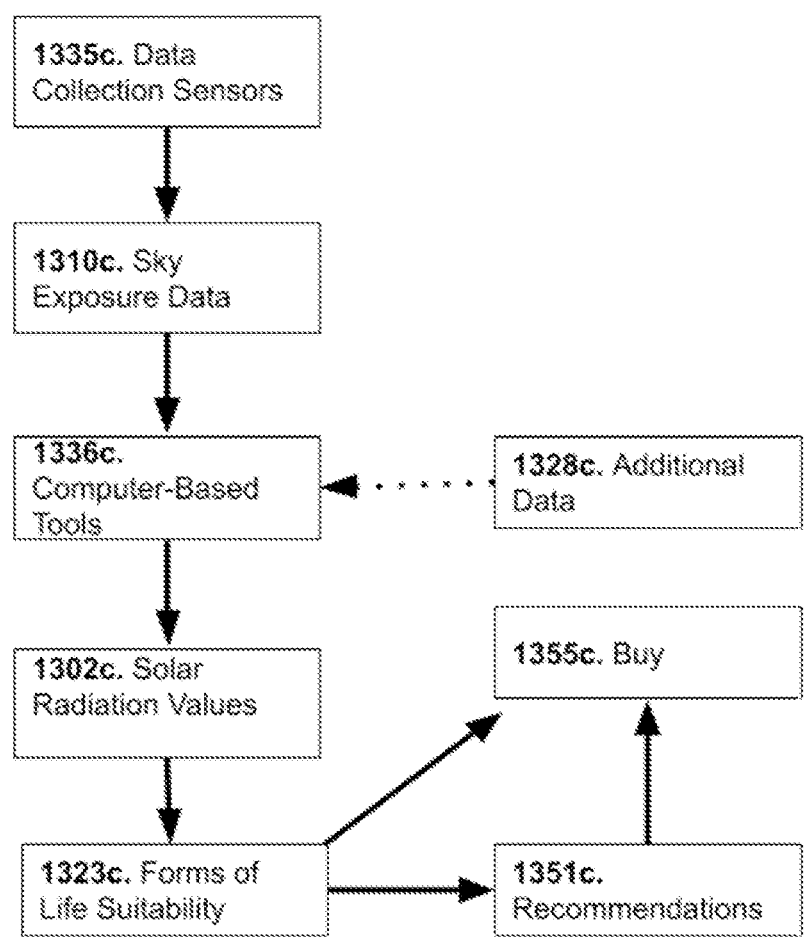
FIG. 13C illustrates a data flow example for purchasing forms of life and recommendations.

FIG. 13C illustrates a data flow example for purchasing forms of life and recommendations. One or more Forms of Life 1323*c* and/or recommendations 1351*c* may be Purchased or Bought 1355*c*, and may be presented (e.g. to a user) before and/or after data collection sensors 1335*c* and computer-based tools 1336*c* have been used to evaluate sky exposure data 1310*c* and assess solar radiation values 1302*c* and forms of life suitability 1323*c* for a location. Additional data 1328*c* may also be considered. A purchase may be a one-time transaction or may be a subscription, and may occur on an app or e-commerce marketplace, may be a service, may be presented with augmented reality, virtual reality, and other mediums of communication.

Figure 14:
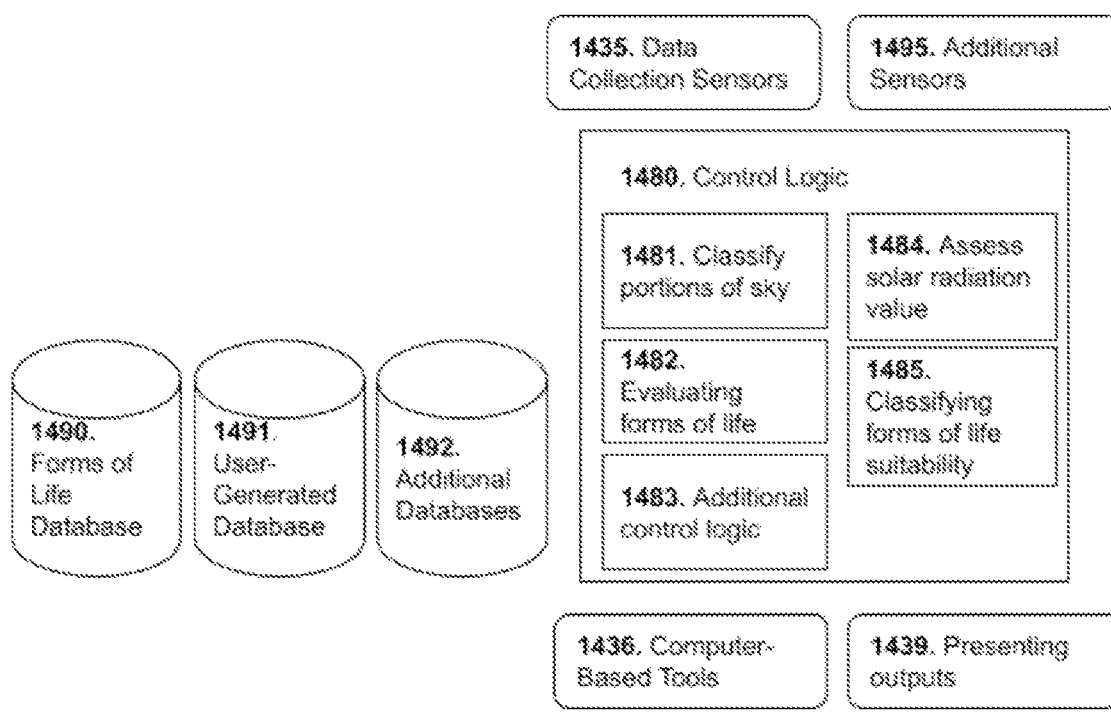
FIG. 14 illustrates a system to evaluate one or more forms of life and classify form of life suitability.

FIG. 14 illustrates a system to evaluate one or more forms of life and classify form of life suitability. One or more data collection sensors 1435 are illustrated for capturing sky exposure data, computer-based tools 1436 for evaluating captured sky exposure data. Control logic 1480 may include logic for classifying portions of sky 1481, for assessing solar radiation value 1484, for evaluating forms of life 1482, for classifying forms of life suitability 1485, and may also include additional control logic 1483. Forms of life database 1490, user-generated data database 1491 and additional databases 1492 may also be utilized. Additional sensors 1495 may also be used. Such systems may also consider at least in part one or more assessed solar radiation values, and may present outputs 1439 in various formats, including for remote operation.

Figure 15:
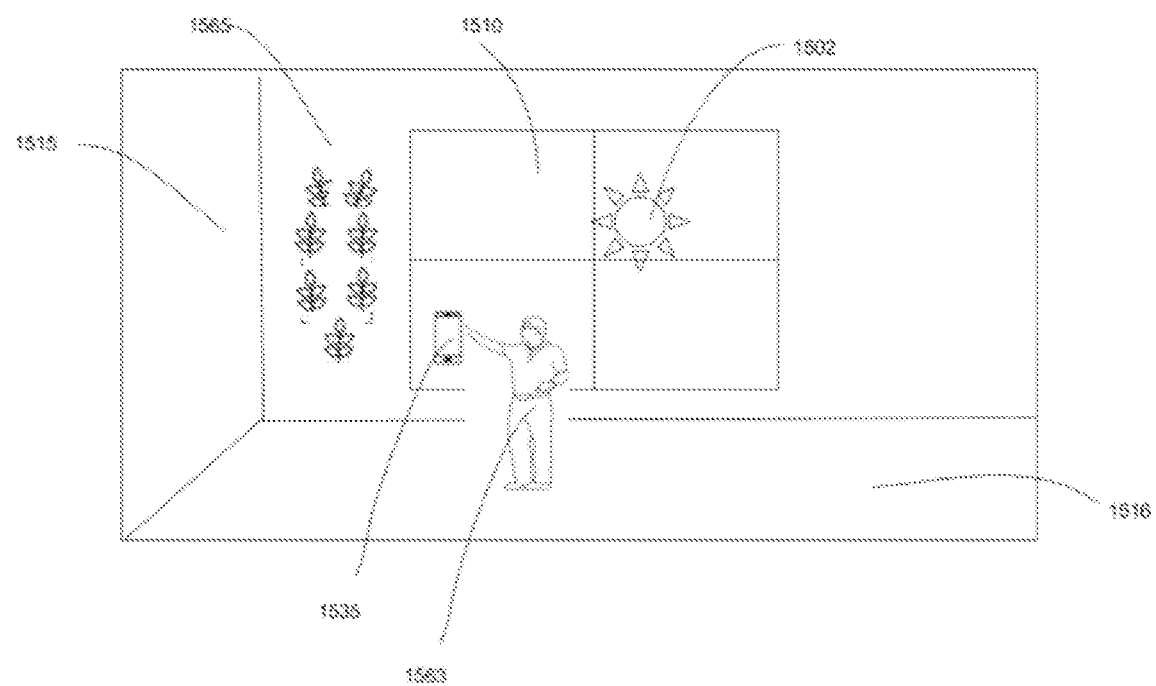
FIG. 15 illustrates an assessment of human wellness factors related to solar radiation values and/or forms of life.
Figure 16:
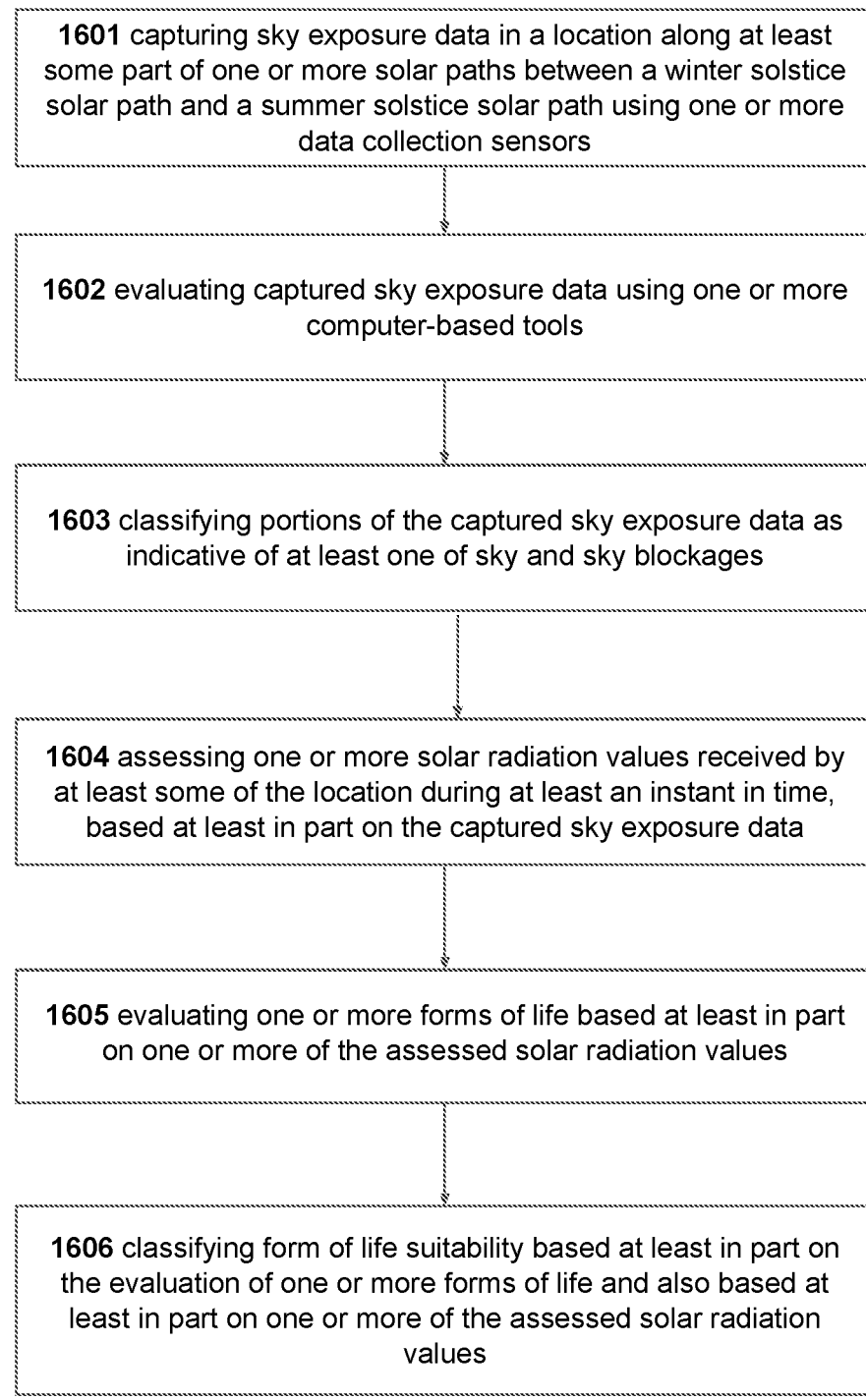
FIG. 16 illustrates a method of evaluating one or more forms of life and classifying forms of life suitability for a location.

FIG. 15 illustrates an assessment of human wellness factors related to solar radiation values and/or forms of life. Illustrated here is an indoor example of user 1563 assessing for human wellness factors, related to one or more of the evaluation of forms of life and a solar radiation value 1502. By way of nonlimiting example, the system may be used to assess how forms of life 1565, for instance plants, provide benefits such as improving air quality or perceived happiness. The system may also be used to assess if the location has solar radiation values optimal for human wellness. The system may also take into account other sky 1510 blockages such as walls 1515, floor 1516, and may quantify the quality of those conditions with image data and any other additional data. FIG. 16 illustrates a method of evaluating one or more forms of life and classifying forms of life suitability for a location. FIG. 16 illustrates: 1601 capturing sky exposure data in a location along at least some part of one or more solar paths between a winter solstice solar path and a summer solstice solar path using one or more data collection sensors; 1602 evaluating captured sky exposure data using one or more computer-based tools; 1603 classifying portions of the captured sky exposure data as indicative of at least one of sky and sky blockages; 1604 assessing one or more solar radiation values received by at least some of the location during at least an instant in time, based at least in part on the captured sky exposure data; 1605 evaluating one or more forms of life based at least in part on one or more of the assessed solar radiation values; and 1606 classifying form of life suitability based at least in part on the evaluation of one or more forms of life and also based at least in part on one or more of the assessed solar radiation values.

Evaluating one or more forms of life. Evaluating one or more forms of life refers to considering at least basic elements necessary for any one or more forms of life, potentially including flora, fauna, fungi, and bacteria, to survive, thrive, grow, and achieve other conditions. It may refer to forms of life at any level of hierarchy of biological classification. For example, it may refer to a genus of Calathea or a specific species the Calathea makoya. Some exemplary forms of life may include monarch butterflies, plankton, oak trees, seaweed, seeds, milkweed (Asclepias), banana slugs, pipers, giraffes, gorillas, humans, fish, corals, mangroves, fire ants, and polar bears, mycelium, coffee plants, carrot seeds, and many other forms. More than one form of life may be considered as a system comprising of basic elements necessary to survive. Basic elements may include sunlight (as may be quantified by solar radiation values), water, soil, oxygen, temperature, humidity, carbon dioxide, food, or shelter. The method of evaluating may use computer-based tools and may use data collection sensors to capture sky exposure and solar radiation data. It may also consider additional data. There may be ranges of biological needs, for instance a Pilea peperomioides may survive for some period of time with draught but she will live more optimally with consistent watering, which may enable her to produce many baby Pilea peperomioides, once propagated.

Classifying form of life suitability. Classifying form of life suitability may refer to different means of describing relationships between one or more forms of life and a location's conditions (including, preferably, at least sky exposure and solar radiation values). Suitability may be described as a binary yes or no, or as a more detailed description of information such as a compatibility score. Or may include the extent to which a form of life is viable, will it thrive, survive, flower, propagate, grow, die, go dormant, create offspring, have yellowing or browning leaves, sunburn, sun damage, shrivel, rot, mold, get diseased, stay healthy or have other trouble. It may also describe one or more qualities of a form of life, such as happiness, calm, safety, productivity, creativity, collaboration, and competition with other forms of life. It may include an expected productivity score such as anticipated yield or growth for example an estimate of 12 inches of growth or flowering 4 times, or producing 80 lbs of food, over a period of time. It may also indicate a period of time for the suitability. For example, a *Ficus lyrata* may survive in a location seamingly suitable for an estimated 60 days, before facing challenges. Or an Oak Tree may thrive in a location for decades. It may present different levels of suitability based on the forms of life, and lifecycle. It may also include suggestions to improve suitability, for example a *Ficus elastica* may stay in this location for 80% of her time, but to maintain this level of health status would need to exist in a disparate location for 20% of the time (an example of taking a sun walk).

Location. Location may refer to any place a user is interested in evaluating using one or more data collection sensors, which may be positioned in that location. Dimensions of a location can vary greatly, depending on the field of view or data collection sensor type, for example a mobile device is likely to have a more limited field of view than a satellite or drone. Location may also reference a position or placement within a place. It may refer to an entire city, a building, portions of a room, portions of a windowsill, parts of a garden, a hanging shelf, or anywhere on the planetary surface. It may be in a cave, on a mountain top, inside homes and offices, in public or private parks and gardens, jungles, above or below the water surface, tree canopy, rooftops, fields, or other terrains. A location may change over time and in some instances historical, current, or predictive location data may be most relevant for the evaluation and classification of forms of life. For instance, a tree warden may be interested in trying to understand why a partial area of trees have been diseased and may need to consider archived data about the location where there were more or less sky blockages which would influence the solar radiation values and classifying forms of life suitability. A location may be indoors or outdoors.

Assessing. Assessing may refer to estimating a quality or significance of solar radiation values for a location. It may be quantitative or qualitative. It may also weigh the statistical significance to one or more values. Further, it could include a judgment that additional values need to be collected to improve the reliability or accuracy of the estimation. It may be presented with certainty or with a qualifier such as 70% accurate. It may be performed in real-time, predictively, or by using historical solar radiation values or location data. An assessment may be saved, shared, presented or modified over time. For example, an assessment may be stored in a database and shared with one or more users at a future date.

Solar radiation values. Solar values may take many forms to describe a quality or quantity of light. Some exemplary forms include solar radiation, solar irradiation, the intensity of light, wavelength of light, KWh, including broad spectrum (not limited to visible light), electromagnetic radiation, radiant energy, radio waves, microwaves, infrared, (visible) light, ultraviolet, X-rays, and gamma rays and many include other values, including anything that can be measured from light. Based at least in part on sky exposure, for at least some instant in time.

Period of time. Period of time may refer to an instant or instance in time during which one or more solar radiation values are collected in a location. Some exemplary periods may include milliseconds, seconds, minutes, hours, daylight time (the time between sunrise and sunset at a location), days, weeks, months, growing seasons (length of a growing season may vary for a location), years, decades, lifetime, lifetime of a form of life, and other time values. A period of time may be current, historical and/or future. It may even combine several different measures of time. For example, current solar value data from 2019, historical data from 2018 and predictive solar value data for 2020 may be combined. It may also refer to other methods of measuring periods of time by use of sundials, hourglasses, water clocks, pyramids, sun, moon or planetary position.

At least an instant in time. At least an instant in time may refer to many different time periods which may be used in evaluation and other processes. At least an instant in time may capture an instant or current or moment in time, or could capture periods of time longer than an instant, for example, a minute, a day, a week, a year, a season, and other possible periods of time.

Sky exposure data. Sky exposure data may take many forms, and may include any sky data that can be detected from a location that comes from above the surface of earth (or a reddish or non reddish planet). In addition to sky, sky exposure data may include forms of clouds, air pollution, greenhouse gases, ozone, smog, atmosphere, space debris, precipitation, atmosphere, stars, moon(s), our sun, planets, birds, planes, blimps, lightning, aurorae, solar winds, or many other forms, many of which may vary with time. It may also consider the quality of the sky exposure data.

A solar path. A solar path is a relative path the sun takes over a period of time from the perspective of a location. Some examples of this include, from a location, we can see the solar path, beginning at sunrise towards the east and setting at sunset towards the west. It may also refer to everywhere the sun passes over a calendar year. The solar path may include the path from sunrise to sunset and from the winter solstice to summer solstice. The solar path area may be different in various locations. For example, at the equator, the solar paths are narrower than at New York City's latitude.

Winter Solstice Solar Path. Winter Solstice Solar Path may refer to the lowest solar path of a year from a location. It may also refer to the lowest path the sun takes in the sky. It may change according to where a user or Data Collection Sensor is oriented or located. For example, in the Northern Hemisphere, the winter solstice is in December, while in the Summer Hemisphere, the winter solstice is in June. It may also refer to an actual or predictive solar path.

Summer Solstice Solar Path. Summer Solstice Solar Path may refer to the highest solar path of the year. It may also refer to the highest path the sun takes in the sky. It may change according to where a user or Data Collection Sensor is oriented or located. For example, in the northern hemisphere, the summer solstice is in June and in the southern hemisphere the summer solstice is in December. It may also refer to a predictive or actual solar path.

Data Collection Sensors. Data collection sensors may include many different types of sensors that can sense data for data collection. Some exemplary forms may include mobile phone sensors, camera sensors, GPS, Gyroscope, Accelerometer, Magnetometer, Proximity Sensor, Ambient Light Sensor, Light Sensors, UV, Meter, Microphone, Pedometer, Barcode/QR Code Sensors, Barometer, Thermometer, Air Humidity Sensor, Geiger Counter, LIDAR, Ozone Monitor, Glass Electrode (Ph), Magnetometer, Photodetector, Photomultipliers, irradiance meters, wind speed sensor, Spectrometer, Infra-red, Visible-light photon counter sensor and other sensors, Moisture sensors, and Radiation sensors. They may also include user-input data from text or audio through a user-interface. It may include additional sensors.

Evaluating, e.g. captured sky exposure. Evaluating may take many forms and may refer to one or more steps or processes taken to calculate, organize, categorize, understand or make use of sky exposure information. Examples of this may include the use of one or more computer-based tools, such as sky detection algorithms, non-sky detection algorithms, machine learning, segmentation, artificial intelligent, or LIDAR to detect which pixels or other parts of image data are sky, and which are sky blockages. It may also include other evaluation methods.

Computer-based tools. Computer-based tools may take many forms. Some exemplary forms include machine learning, computer vision, Long short-term memory (LSTM), Convolutional Neural Network (CNN), Support Vector Machine (SVM), computer vision, artificial intelligence, segmentation, hierarchical, edge detection, neural networks, quantum computing, Blockchain, distributed ledger, and many other forms of computer-based tools.

Classifying portions of the captured sky exposure data. Classifying portions of the captured sky exposure data may include the labeling of one or more types of image data, for example to show visible sky and sky blockages. This may include a binary assessment such as sky, % not sky, or a more detailed reference discussing the qualities of the sky exposure. The classification may utilize different computer-based tools, such as computer vision and may depend on the location and conditions. Examples of these conditions include, varying times of weather, time of day, color of the sky, landscape, and more. They may also include identifying different portions of image data. One example may be that a user captures sky exposure data of all of the visible solar paths over a calendar year (from winter solstice solar path to summer solstice solar path and from sunrise to sunset) in a location. Classification can then be used to assess and predict the solar radiation values over the course of the entire year. Including calculating total solar radiation for a location as well as calculating for another period of time, such as a day, growing season, form of life's lifetime and more.

Indicative of. Indicative of may refer to the representation or suggestion of sky or sky blockages, as captured by a data collection sensor.

Sky. Sky may refer to the atmosphere and outer space seen from a planetary surface, such as Earth, associated with a location. It may encompass anything above the surface of earth (or another reddish or non reddish planet).

Sky Blockages. Sky blockages may take many forms and may include anything on or above a planetary surface that may block the sky from the perspective of a location, such as buildings, trees, plants, flowers, other forms of life, cranes, mountains, telecommunication towers, vehicles, space stations, and other infrastructure. It may also include obstacles that are not on the planetary surface. Exemplary sky blockages may include birds, airplanes, planets, space debris, blimps, helicopters, hot air balloons, heavy smog, solar winds, greenhouse gases, precipitation, moon(s), our sun, aurorae, air pollution, and other forms of blockage. Sky blockages may be more permanent such as building or more temporary such as flying bird, this may also be taken into consideration in the classification.

Presenting (to a user). Presenting to a user may take many forms. Some exemplary forms may refer to sharing information with a user through a user interface, which may be visual, audio, haptic, brail, and other methods. If visual, augmented or virtual reality interfaces may be used. Some exemplary forms may include an interface, immersive experience, media, audio, video, or any other form of communication or delivery. It may be presented in the physical world, for example a laser projection on the sky, use augmented reality, for example showing a user a solar path while collecting data via a data collection sensor, or shown in virtual reality. It may also be shared autonomously or directly with a user via computer-based tools. It may appear on a phone screen, headset, audioset, home system, haptic device, or other hardware or software. It may also refer to additional forms of presenting.

Instructing. Instructing may take many forms. Some exemplary forms may include guiding a user through an interface, experience, media, audio, video, or any other form of communication or delivery. It may be seamlessly blended with virtual objects in the real-world, immersive, engaging, and responsive to user initiated actions, use augmented and/or virtual reality showing a user a solar path while collecting data via one or more data collection sensors, and may also be presented in the physical world, for example a laser projection on the sky. It may be visible to a user. It may also be shared autonomously or directly with a user via computer-based tools. It may appear on a phone screen, headset, audioset, home system, haptic device, or other hardware or software. It may refer to additional forms of instructing such as gestures or movement. It may take feedback from a user and be responsive to additional data inputs. It may be different instructions based on time of day, location, user type, direction, or other variable data such as preferences.

Orient. Orient may refer to moving or rotating or redirecting one or more data collection sensors, changing the field of view, viewpoint, of one or more data collection sensors. For example, rotating a mobile device with data collection sensor around a central-axis, or panning such a device across a panorama, to capture additional portions of solar path and sky exposure data. It may refer to more significant re-positions of data collection sensors such as the case with a drone or satellite which may be capturing data across larger terrains. It may also refer to different instances in time where additional data capture is required, such example during a different year or seasons or alternate position to get a deeper or more accurate view of the location under assessment.

Additional portions of the solar path. Additional portions of the solar path may take many forms, and include additional data captured along one or more solar path, such as a current solar path, summer solstice solar path, winter solstice solar path, or equinox solar path by one or more data collection sensors. Examples may include a user taking additional image data of a solar path, which may include one or more still images, one or more panorama images, one or more videos of a different section of a solar path or similar solar path at a different instance in time. It may also take the form of a user inputting qualitative information about a solar path, for example estimating how many hours of direct light a location may receive over some period of time (e.g. per day, per season, or per year) or if a location may receive any direct light at all. It may also refer to capturing portions of image data, to understand if other paths of solar radiation may affect a location, such as mirrors or windows reflect or in the case of location with more than one window.

Capture additional sky exposure data. Capturing additional sky exposure data may include taking additional image data, and examples may include a user taking additional image data of a sky exposure, which may include one or more still images, one or more panorama images, one or more videos of a different section of the sky at a different instance in time along one or more solar paths, and may refer to pointing one or more data collection sensors towards another part of a solar path or more. It may utilize the same data collection sensor as initially used, for example a mobile device or it may utilize one or more additional data collection sensors such as via drone capture, satellite capture, etc. This may happen at a different instance in time, or immediately following the initial capture of sky exposure data. It may also refer to taking an additional data collection of the original sky exposure, but in a different instance in time, for example on a sunny or cloudy day to evaluate variability.

Estimating (insurance). Estimating may refer to evaluating a price, value, quality, ownership, quantity, benefit, or other value that may be associated with forms of life in the past, present or future. Estimating may be for a guarantee, time-based coverage, money-back guarantee, or insurance of parts or all of one or more forms of life. It may consider one or more insurance-related parameters and may also consider additional data.

Insurance-related parameters. Insurance-related parameters may include data related to forms of life or solar radiation values, for the statistical and mathematical calculations to predict how likely an insurance applicant will be to make a claim on their policy. Parameters may include the form(s) of life, and qualities such as age, fragility or fussiness, dimensions, including height, weight, volume, value, productivity, usability, quantity that remain (i.e. especially in the case of extinction of vulnerable forms of life), and any other data parameter that may influence assessing a form of life for insurance-related purposes. For example, Maidenhair Fern (*Adiantum aethiopicum*) are fussier and more challenging to care for than a Sansevieria and thus more likely to cause an insured to make a claim on their policy. Another example, as it relates to humans may include parameters such as known existing mental or physical health conditions.

Incorporating additional data. Many forms of additional data may be incorporated and utilized. Some exemplary forms include time of year, time of day, ambient light, indirect light, spatial measurements, infrared, imagery data, pollution and air quality data, productivity data, care plan data, health status data, health solution data, medium enhancing data, purchasing history data, land or form of life ownership data, age of form of life, data on volatile organic compound (VOCs) such as benzene, acetone, toluene, formaldehyde, dust data, presence of glysophates or other agricultural compounds data, location of form of life, material data, model data, plan data, greenprint data, solar calibration data, other solar radiation methodology data, human wellness data, user preferences data, oxygen data, carbon dioxide data, temperature, humidity, lux, lumens, footcandles, satellite imagery, GPS, location data, direction, water quality, soil quality, gyroscope, user data, weather data, historical data, predictive data, microbial data, performance data, other user-generated data, other forms of life data, e-commerce data, including availability, accessibility, price, and other considerations, accessory data, services data, appraisal data, conditions data, other forms of life data, and any other additional data that may be relevant, useful or supplemental. Additional data may be collected by one or more data collection sensors, may be collected through computer-based tools such as databases, APIs or algorithms, machine-learning, or artificial intelligence. Additional data may be considered at any point in the method or system and may be introduced episodically or on a one-time basis. Additional data may be input by a user and/or may be asynchronously incorporated.

Conditions data. Conditions data may refer to conditions that impact forms of life. Some exemplary conditions data include solar radiation values, weather, temperature, season, soil composition, ground temperature, microbial activity, water composition, topography, terrain, spatial characteristics, humidity, ozone, heavy metal level, pH level, air pollution historical climate conditions, predictive climate conditions, salinity, and other data that may influence forms of life.

Recommending a customized care plan. Recommending a customized care may take many forms. Some exemplary forms may include one or more activities related to the form of life, also known as hortophilia. Such activities may relate to care, maintenance, planning, growth, implementation. Exemplary activities may include watering, feeding, fertilizing, adjusting solar exposure, repotting, adding top soil, pruning, soil analysis, collecting samples of water or soil, rotating forms of life i.e. (rotating the position of a plant periodically so different portions receive sunlight, cleaning forms of life (i.e. washing or wiping down leaves), changing, modifying or altering growing conditions (i.e. adding supplemental lighting, removing sky blockages, adjusting temperature, adjusting humidity, removing or adding complementary or incompatible surrounding forms of life. For example, if an indoor Sansevieria "snake plant" is in a location with 200 lux it will need different care than the same plant in 8,000 lux. The watering, plant nutrients, repotting schedule, and other parameters may be different in each location. A customized care plan may be dynamic to other factors such as adding or removing forms of life within a care plan, current weather, precipitation, wind, frost, heatwave, pests, infestations, as well as user preferences, performance data, and other user-generated or additional data. A care plan may differ during the lifecycle of a form of life (i.e. care may be different for an acorn than a mature oak tree). It may include activities such as sowing (such as by hand, system or remote-operation), harvesting (such as by hand, system, or remote-operation), propagating (i.e. division, cutting, grafting, budding, servering, rooting, layers, micropropagation, stolons or runners, twin-scaling, striking or cutting), pollinating (such as by introducing pollinators to a location, or by other methods), planning, and making structural, material or spatial modifications. Care may be preventative or diagnostic. In the case of diagnostic, it may utilize a history of data about the forms of life, solar radiation and maybe conditions data, and additional data points including user-generated data, and other variables. Care may be modified or customized by a user to adapt to their schedule, skills, or optimized for efficiency, outcome, yield or other objective. A predictive care model can be used to compare care plan scenarios on a level of scale, including for urban cities, governments, farms, greenhouses, or for large corporations. Care activities may be delegated and shared among a group, team, family, country, or across an organization. The completion of care tasks may be presented to the other members so they do not complete the same task again.

Care activities may be tracked in a care log visible to a user or not, with details including period of time and maybe observations on a form of light. This form of user-generated data, may include image data, video data, audio data, or textual data. Care may include details such as ½ cup of water or more general such as identifying a day for a plant to be watered. It may or may not recommend specific products or services to use such a branded watering can or branded fertilizer. Care plan may be responsive to user input (i.e. updating watering schedule if user waters form of life on a different day than initially recommended, or user performs a health status assessment). It may adjust at any time to support the form of life, in their next phase of growth, based on observations (i.e. the onset of yellow or browning leaves) or to incorporate health solution recommendations. For instance, a Chlorophytum comosum Spider Plant that has been assessed by a user or computer-based tool maybe using data may be recommended a treatment of Neem oil applied episodically. A care plan may incorporate other feedback loops, which may take many forms such as episodic image data to monitor form of life. A care plan may remind a user to perform care activities, via notifications, messages, emails, phone calls, calendar, sensors, or any other method of communication. A form of life may also prompt a user to follow a customized care plan. A care plan may consider additional variable outside of form of life such as resource and input management, and may optimize for water conservation in regions such as California or others where water use is sensitive. A care plan may predict or estimate the productivity of one or more forms of life, with computer-based tools. It may also consider mortality rates of forms of life, to assets the span and scope of a customized care plan. It may include information such as stress to form of life, over or underexposure to solar radiation, exposure to toxins, exposure to poor water quality.

Mapping. Many forms of mapping are contemplated. Some exemplary forms include overlaying solar radiation values and forms of life suitability onto a blueprint, floorplan, 3D rendering, or other visual or statistical model or another model. Mapping may be done manually, by computer-based tools or by a combination. Mapping may show where and when different forms of life may exist, flower, thrive, and other data. It may show how solar radiation values can impact care of forms of life and other examples. Also may be described as overlaying data over a model.

Model. Models may take many forms. Some exemplary forms include a 3-dimensional representation, a floorplan, greenprint, blueprint, 2D representation, diagram, illustration, numerical table, or one or more databases. It may use augmented reality, virtual reality, or be in the physical world. It may be compatible with other software and models, for example for design, drafting, CAM, engineering, analysis, rendering, animation, architecture, interior design, landscaping, urban planning and more. It may be presented in different formats for example augmented reality, virtual reality, be a portion or part of other models used by industry experts and professionals such as architects, interior designers, urban planners, landscapers, for conservation, or restoration. It may include the overlay of other recommendations, such as traffic data, city sprawl, sewage lines, fiber optic cables, WIFI, 5G, future communications networks, and more. It may be converted or exported into different file formats for easy sharing. It may be used to assist in biophilia design and to ensure the care and maintenance of forms of life are feasible and considered in advance of implementation. It may be added to or modified based on changing parameters such as budget constraints, or changing objectives. It may be used to simulate form of life growth and changing conditions overtime, such as rising temperatures, and ecosystem considerations. It may be used to plan, map, and inform decisions, inspect details, inspect parameters, incorporate spatial or material considerations. It may include indoor or outdoor data. It may be useful for agriculture, archeology, conservation, geology, land use planning, surveying, transportation, wind farms, solar farms, other renewable energy locations, and cell tower deployment. Recommendations of all types and forms of life may be purchased directly from a model, saved, or favorited. A model may be continually updated through episodic data sensor capture such as real-time weather or actual growth rates, or forms of life productivity values.

Implementing. Implementing may take many forms and may refer to putting into effect parts or all of a model. Some exemplary forms of implementing may include planting, fertilizing, making structural modifications, adjusting conditions, adding or removing forms of life, performing recommended services (such as tree installation or tree removal), or care activities (such as watering), adding control or growth enhancing mediums and many more. Implementing may be performed by humans, computer-based tools, or remote-operations.

Capturing Additional Sky Exposure Data. Capturing additional sky exposure data may take many forms and use one or more data collection sensors. Some exemplary forms include taking supplemental image data (which may include one or more still images, one or more panorama images, one or more videos) of additional areas of the sky area or celestial dome. This additional sky exposure data may be taken to cover additional portions of the area or to capture the same area at a different instance in time, when the sky exposure qualities may or may not be the same as at another instance in time.

Image Data. Image data may take many forms. Some exemplary forms include one or more still images, one or more panorama images, one or more videos which may or may not be taken along a solar path. Image data may be captured by one or more data collection sensors or may be processed through several forms of computer-based tools.

Improving performance. Improving performance may take many forms. Some exemplary forms may include increasing the yield, rate of growth, remediation, resiliency, the likelihood of flowering, ability to sequester carbon, nutrient uptake, water uptake, aeration, aesthetic, taste, smell, nutritional composition, color, pattern, texture, shape, form, health benefits, ability to photosynthesize, calmness, digestion, metabolism, speed, endurance, agility, pest resilience, drought resilience, strength, wind resilience, flooding resilience, and many other forms.

Utilizing additional data. Utilizing additional data may take many forms, many of which have been outlined under incorporating additional data. In the case of user preferences data, some exemplary forms may include price, reviews, dimensions, harvest-time, care-complexity, pet-friendly, child-safe, travel-friendly, edible, flowering, rare, sustainable, organic, deer-resistant, pest-resistant. Additionally, user preferences may include data inferred by user activities such as existing flora and fauna, GPS location, seasonality, and availability of recommendations. Additionally, user preferences may include data learned from the user, such as when they want to order, provide care, and their habits. The use of additional data may be to further customize or improve an assessment, evaluation, classification, or recommendation by computer-based tools and data collection sensors.

Disparate locations. Disparate locations may refer to more than one location. These disparate locations may be within the same room (i.e. a southern facing windowsill and a northern facing windowsill) or may vary by significant geography such as a garden in Brooklyn, N.Y. and another garden in Oakland, Calif. While there may be significant differences between these disparate locations there may be one or more similarities. Similarities here may include solar radiation values, forms of life classifications, soil composition, water quality, weather patterns, enhancing mediums, the same user, or a purchase of the same for of life or recommendation.

Recommendations. Recommendations may refer to actual forms of life (such as flora and fauna, bacteria, fungi, humans), products (such as gardening tools, systems, planters, accessories, watering cans, and other products), services (including maintenance, installation, design, implementation, repair, gardening, landscaping, removal, regeneration of the soil, lawn care, etc.), activities (such as kokedama, Macrame, terrariums, Fairy Gardens, floral design, foraging, creating pollinator habitats, and or DIY activities), and solutions (such as modifying conditions, support for ailing plants, etc.), methods (such as moving the plant, watering, caring for etc.), condition modifications, such as opening a window, removing a blockage such as a wall, adding or reducing supplemental lighting, adjusting temperature, adjusting humidity, a new planter. May include seeding saving recommendations; may include sharing recommendations with others. It may refer to recommendations of other disparate locations that relate to a location, for learning or performance uses. May be constrained by the available space, season, other conditions data, user preferences and availability of recommendations in a marketplace or platform.

Quantifying. Quantifying may take many forms. Some exemplary forms include a numerical value, description, or classification of productivity, such as yield, which may be measured in pounds, CO2 sequestration as measured in pounds or tons, or growth rate as measured in inches. It may capture one or more productivity values into an equation.

Productivity value. Productivity value may take many forms and refer to any value derived from a form of life. This may include, toxic remediation value, food production value, air improvement value. yield of a vegetable in lbs, health benefits in VOC reduction, tons of CO2 sequestered, happiness index, creativity index, wellness value, and many others.

Medium Enhancing Recommendations. Medium enhancing recommendations may take many forms. Some exemplary forms include the suggestion of one or more mediums to enhance or improve forms of life. For example, soil, soil amendments, nutrients, fertilizers, forms of life that support other forms of life, such as worms, ants, and praying mantis, and others. They may also refer to mediums that control other forms of life such as weeds or pests, that may be competition. Other forms of medium enhancing recommendations may include removing existing elements such as the removal of heavy metals, poor water quality, or other unwanted or unhelpful substances present nearby the forms of life location.

Assessing Health Status. Assessing health status may refer to the assessment of a form of life's health. Assessments may take many forms and consider data and variables from images, user data, soil testing, water testing, pollution testing, visual biomarkers such as leaf pigmentation (yellowing leaves, browning leaves, etc.), inability to flower, stagnant growth, shriveling, wilting, losing leaves, changes to chlorophyll content, and other biochemical processes which may be less visible, and many other forms to classifying and understand a form of life's current, past, or future health. It may also consider one or more solar radiation values or conditions data, or nearby forms of life data.

Health Solutions Recommendations. Health solutions recommendations may take many forms and aim to address the health condition of one or more form of life. Some exemplary solutions include water filtration, use of rainwater, nutrients, fertilizer, pest control, fungicide, pesticide, adaptations to lighting and other conditions, pruning, changing soil, moving location (or placement) of forms of life, and more.

Appraising. Appraising may include looking at various variables in order to estimate a value for a form of life. Variables may include, age, size, health, benefits, productivity, health status, location, environment, and others. May include additional variables such as number of similar or exact forms of life (i.e. rare or endangered forms of life). It may also consider market rate, monetary values, proximity values, benefit values, climate change mitigation value, biodiversity value, pollinator value, value to any other form of life and other values.

Training Recommendations. Training recommendations may include instructing a user on how to perform tasks. Some exemplary forms include, repotting a plant, deadheading, washing a dog, assembling a raised bed garden, pruning a bonsai, installing a plant wall, removing an infestation of aphids, or many other recommendations. These recommendations may be delivered in many different forms. Some exemplary forms include text, voice, audio, augmented reality, virtual reality, in person, on a mobile device, in learning modules, or on the job training.

Forms of life caring-skills. Forms of life caring-skills may refer to any ability that relates to supporting forms of life. Skills may vary by complexity. Some exemplary forms of life caring skills may relate to specific forms of life and to the difficulty level of care for the species. For example a Bonsai tree may be harder to care for then a Sansevieria. Additionally there may be differences in complexity of the care activities, such as watering may be easier than repotting. Other forms of life caring-skills may include pruning, watering, cleaning, propagating, feeding, fertilizing, finding ideal solar radiation conditions, and other skills.

Structural modification recommendations. Structural modification recommendations may include removing window blinds, curtains, changing position of windows, walls, other barriers, trees or other vegetation, fencing, and others.

Enabling. Enabling may refer to making something available to. This may include providing an e-commerce, marketplace or other digital means of availability. It may also include recommending local retail locations that can fulfill a purchase experience. It may also include other opportunities or experiences.

Purchase and Sale. Purchase and sale may refer to the ability to purchase goods or services, as well as sell goods and services, including forms of life or recommendations. It may take many forms, such as a one-time transaction, a subscription, it may bundle, package or customize the goods and services for purchase or sale, it may enable users to return or exchange items, or add coverage or insurance to the purchase or sale items. It may be presented to a user in an immersive experience such as via augmented reality or virtual reality or it may be an in-person transition. It may facilitate connections through a marketplace, including peer-to-peer transactions.

User. A user may refer to an individual, operating system, autonomous, robot, drone, organization, commercial store, person, etc.

Human wellness factors. Human wellness factors may take many forms. Some exemplary forms include level of volatile organic compounds (VOCs), available oxygen, the ratio of people to plant life in a location, accessibility of fresh and healthy food, the amount of solar radiation a location receives over the course of a year or a day. In the example of a year, it may be a proxy for how productive or well a human may be. This could be used by human resources or office designers and combined with other data to assess how light and accessibility to other forms of life, such as plant life may play a role in creativity, mental health, productivity across an organization. It could also be used to understand how solar radiation affects a suntanner, and if the above coconut tree provides sufficient shade as the sun moves along a solar path during the day, by way of example. It may take other forms as well.

Solar Calibration. Solar calibration may refer to a method of calibrating at least one or more of a collection of sensors and computer-based tools in order to understand the real-time solar radiation values reaching a location. It may provide details on refraction by the atmosphere, clouds and more. It may also provide details into weather. Such as cloud density, haze, smog, pollution levels and more. Solar calibration methods may include a collection of sensors measuring the solar radiation values and additional data. An example may include a user taking picture or other image data at the sun. It may include recommending protective eyewear or using a mobile device as sunglasses. This method may enable the prediction of a daily high solar radiation value during varying weather conditions.

Daily High Solar Radiation. Daily high solar radiation may refer to the daily high light level at a specific location. This daily high value may change over the course of the year and will depend on the location. Daily high value may be used as a metric of the daily high solar radiation value of a clear day and sun transit time. This number may be predicted, current, historic data, or some combination thereof.

Quality Assurance. Quality assurance may refer to verifying a form of life has adequate or ideal conditions and a care plan has been established. This could be ideal while considering the supply chain of a form of life, for instance tropical plants are moved from a nursery in Florida to another nursery or warehouse in New Jersey and then to a store or home delivery in Manhattan, N.Y. Verification could take several forms such as user-generated tracking of activities and capturing sky exposure and solar radiation data, it could also happen continuously or episodically for example in a greenhouse, urban park, or farm through image or other data collection sensors. Quality assurance and other data could be captured, stored and saved on a blockchain or on a distributed ledger. For certain forms of life quality assurance may even cross generations of forms of life.

Plant Doctor. Plant Doctor may refer to taking a picture, or other data capture, of all or part of a plant, tree, flower, or other flora and diagnosing issues, and prescribing care. May include plant identification, measurement of growing conditions (potentially including solar radiation values, soil quality, climate, and more), previous plant health data, including diseases, diagnosis, and insufficiencies and may include additional user-generated data such as more image data, qualitative information such as presence of yellowing leaf or other nearby forms or life, or changes to care plan such as extended travel or neglect or insufficient or too much resource addition, such as excessive watering. It may also consider data from disparate location for instance, a migratory path a blight in beech trees.

Additional light data. Additional light data may take many forms and be considered to assess the full light potential of a location (in addition to assessing sky exposure and solar radiation values). Some exemplary forms include solar irradiation, LIDAR, quantity of light, quality of light, Light Wavelength, Flux (Luminous Flux), lumens (lm), watts (W), Candela (cd), lux (lx)—The SI unit of illuminance and luminous emittance, Footcandle, luminance, radiometry, Radiant Flux, Radiant Intensity, Irradiance, Radiance, Luminous flux, Luminous intensity, Illuminance, Luminance, photometry, spectroradiometry, spectral radiance, spectral Irradiance, and may be captured by many forms of data collection sensors such as photometer, such as a luminance meters, illuminance meter, integrating sphere, or spectrometer and many other methods. Additional light data may be used recommended in a customized care plan, a model, and may be incorporated into a form of life care plan dynamically such as during winter months when the solar path is lower and less solar radiation may be received through a window indoors.

Evaluating solar radiation and other light values, e.g. for real estate and other purposes. Evaluating solar radiation values and other light values refers to the consideration of solar radiation values at any point in the lifestyle of construction, real estate development, urban development, planning, design, or similar or related, which may improve the conditions for humans and other forms of life. For example, it may refer to prioritizing sky exposure to as many locations as possible within an office environment. Or determining the need to increase or decrease lighting to improve the conditions for one or more forms of life. It may inform recommendations such as bringing more plants into a building or specific types of plants. It may refer to designing architectural structures where forms of life come first, such as putting flora at the center of the design process. It may refer to classifying different zones or zones for different types of productivity for a form of life. Such as a room with a certain solar radiation values and forms of life as optimal for creativity or another disparate location as optimal for productivity. It may also be used for zoo design or other places that house forms of life.

Identifying forms of life. Identifying forms of life may refer to a process of naming or recognizing a form of life, possibly using one or more computer-based tools such as visual recognition, computer vision, image segmentation, LIDAR or many other tools. It may be done before or after classifying form of life suitability to a location. Identifying forms of life may also enable a user to purchase the identified form of life. For example, a user may be in a restaurant or walking down the street, identify a form of life, and be presented the option to purchase it. May be presented through a user-interface, in augmented reality, virtual reality or many other formats.

Information on forms of life. Information on forms of life may take many forms. Some exemplary forms include an immersive, augmented or mixed reality experience that labels different forms of life and presents a user with more information. For example, about the needs of a form of life or the last time a plant for instance was watered. This could be useful in the case of customized care and delegating and sharing care activities with more than one person. It may appear a hovering symbol above a form of life, for example, or instruct or guide a user on what to do or what steps to take. It may also include data on productivity, for example giving a user the ability to walk through a farm or other area and see the productivity or yield of different forms of life and considering at least one or more solar radiation values.

Gamification (e.g., of forms of life suitability). Gamification may take many forms. Some exemplary forms include introducing elements of game playing such as point scoring, competition between others, rules to play, surprise and delight, for example as it relates to forms of life suitability. For example, a user may get more points or rewards or accomplishments or similar as they care for different forms of life, or for a period of time, or they care for rare forms of life, or they perform one or more harder care activities such as removing aphids from a spider plant. It may also refer to identifying one or more forms of life as a competition, similar in ways to Pokemon Go, for example, but for real life flora and/or fauna. One or more computer-based tools may be used to implement these elements.

Forms of life playlists. Forms of life playlists may refer to a category of forms of life. Examples of this may be plant playlists such as Pollinator Plant Playlist that is focused on plants that support local pollinators. It may also be categorized by individual or organizations recommendations of what to plant according to a location and conditions. For example, a chef, farmer, DIY gardener could compile a plant playlist of vegetables, grains, fruits and other food crops that they would recommend a user grow and cook with. It may also include recommendations relating to non-governmental organizations (NGO) and/or a government's decisions regarding life forms that may be grown at one or more locations. A plant playlist can be explored and it can also be used to provide specific recommendations of what can be grown based on solar radiation values and other conditions data.

Supplemental Lighting Systems. Supplemental lighting systems may refer to understanding lighting conditions, and to determine the need to increase or decrease supplemental/artificial lighting for indoors or outdoors. May include but is not limited to growing lights for plants or other growing systems, but may also be relevant for art, photography and beyond; May be used in real estate, landscaping, construction, manufacturing and other applications, and in design processes.

Plant(er) Size. Plant(er) size may include measurement of forms of life and forms of life accessories and conditions. Examples may include using augmented reality and computer-based tools to measure the size of a planter, plant, raised bed, etc. This may be used to inform care and other recommendations. For example the size of the pot and plant may inform their nutrient and watering needs.

Greenprint. Greenprint may take many forms. Some exemplary forms include a map, diagram, or model that classify forms of life suitability or forms of life potential for one or more locations. A Greenprint could capture data for a location such as a bedroom or on a larger scale for example a planet, such as Earth. A Greenprint may or may not include recommendations such as care recommendations, structural recommendations, or estimates for forms of life productivity. It may be especially useful in construction, to understand forms of life suitability during the building, planning or designing process. It may be presented to a user through a user-interface, in augmented reality, in virtual reality and in any other 2D or 3D view. It may appear different based on the user or user preferences, for example, highlighting different elements or proportions of the Greenprint to different stakeholders. For example, a user who cares about beautification may be presented with information and data about the forms of life, such as plants that will bring beauty to the location. A user who cares about management and maintenance may be presented with the operational view and/or customized care plan that may be necessary to maintain the forms of life. A user who cares about infrastructure and materials may be presented with a into the structural modification or materials considerations may be necessary for the forms of life suitability. A user who care about wellness factors may be presented with estimated productivity values such as predictive $CO_2$ sequestration or food yield. These alternate views may or may not be layered on top of an immersive world with real world objects and be selected or unselected at any point. It may take many other forms. It may consider additional data, conditions data, performance data from disparate locations and be implemented in part of in full by one or more remote-operations. It may consider other user preference data such as budget, time constraints, other forms of life, such as a pet dog, or allergies, or use of space data such as traffic patterns and more.

Quantifying Biodiversity (associated with forms of life). Quantifying biodiversity may take many forms and refers to quantifying at least a value associated with introducing a form of life to a location. Could include short term values, long term values, and values representative of different periods of time. It may refer to the process of quantifying benefits or disadvantages of introducing a form of life or speaks to its effects in more detail on other forms of life. This biodiversity data on forms of life may be captured by one or more data collection sensors, for example a drone, satellite, medical diagnostic sensor and evaluated by one more computer-based tools such computer vision, LIDAR, artificial intelligence, or segmentation. It may be combined with solar radiation values, form of life data, conditions data, location data, and additional data of relevance, such as health status data. For example, the introduction of milkweed into a location may show that many new monarch butterflies and other pollinators now call this location home. In some instances, the introduction of species that overly compete with the existing forms of life may cause a reduction in the biodiversity population. Classifying, quantifying, and evaluating the interconnectedness of forms of life may be of value to improving performance recommendations of disparate locations or in future classifications of forms of life. The data may also be processed and saved in a form of life database, care database, location database or other stores of data. This data may be captured for an instance in time or period of time, or episodically. It may also refer to assessing the health status of one or more forms of life. An example would be assessing the microbial diversity of a human before and after exposure to one or more forms of life such as fungi, bacteria, living soil, or other plant life.

Spatial awareness (for location). Spatial awareness may take many forms and refers to data about the dimensions of a location. It may be captured by one or more data collection sensors, such as may be found in a mobile device, and evaluated by one or more computer-based tools, such as augmented reality or computer vision. This spatial awareness data may be considered under conditions data or additional data used to power classifications such as forms of life suitability and other recommendations. It may also reference the forms of life database or care database, for example spatial data may evaluate that a location could only hold a Monstera or a Live Oak Tree for a period of time before the form of life outgrows the location. The nuances of this information may be especially relevant for landscaping design, interior design and restoration to ensure forms of life are not overly competing for space. It may refer to many other spatial qualities.

Evaluating forms of life solutions. Evaluating forms of life solutions may take many forms and refers to assessing and recommending forms of life to address location issues. Some exemplary location issues include flooding, wildfires, storm surges, runoff, landslides, mudslides, volcanic activity, deforestation, earthquakes, tsunamis, and many more. It may use one or more data collection sensors and one or more computer-based tools to evaluate suitability. For example, in a location that experiences flooding, one or more forms of life, such as mangroves, may be recommended as partial flood management. The process of evaluating forms of life solutions many consider additional data such as solar radiation values, land ownership data, forms of life appraisal data, care and maintenance data, productivity data, and other recommendations data. It may evaluate forms of life suitability and compare it to material solutions such as buildings or other infrastructure. It may also consider insurance parameters for forms of life. It may be used to urban developers, homeowners, hospitals, governments, environmental groups, and in many other use cases.

Forms of life database. Plant database may take many forms and may refer to an engine of data associated with one or more forms of life. Some exemplary forms include an indoor plant life database or an outdoor plant life database, which may include historical, current and predictive data about specific forms of life. It may also consider other additional details such as care, location, spatial data, solar radiation values, other recommendations including products and services received by forms of life and productivity values of forms of life. It may include appraisal values, insurance parameters, health status, health solutions recommendations, and disparate location data. Forms of life database may be added to modified and utilized at any part of the evaluation and classifications of forms of life suitability. It may also be accessed as an API for other use cases such as agriculture, farming and many more.

Evaluate ground Image data. Evaluate ground image data may include taking an image of the ground to detect it's status. This may include detecting what the ground is composed of (e.g. if it is soil, asphalt, other surfaces), what forms of life may inhabit an area, or other conditions. It may also include close up image data of soil, e.g. useful to detect soil type and composition from image data.

Circle Method. Circle method may enable a user to measure a location's conditions and assess its potential to support forms of life by combining light readings and other data. This methodology has both indoor and outdoor applications. Here is an indoor example: User stands at a location where they would like to measure for forms of life potential or confirm if a specific form of life should be placed in that location. Indoors, this could be near a natural or artificial light source, this includes windows, doors, skylights, artificial lights, and any atypical source of natural light. Using one or more data collection sensors such as may be found on a mobile phone, a user may move device in one or more circles or another pattern to measure the locations' conditions. This may include using this device to determine real-time light (lux) levels, spatial data (possibly including for example size of window, overhang, distance from light source, etc), direction (to determine the formula of how light will change over the course of a day or year or another time period), weather (e.g. in order to calibrate light readings and understand current lighting conditions), and other variables. This data may be collected and be combined with other imagery- or non-imagery data. Depending on the real time lux value, time of day, spatial data, weather and/or other variables, a modified lux value may be generated that equates to a daily or annual high for that location. Other outputs may be generated as well. These outputs may be used to recommend forms of life, recommendations (including accessories, services, care, and/or confirms one or more forms of life suitability for this location. It may also detect the duration that a form of life may thrive or survive in these conditions, in this location. A data collection sensor can sense data for a location and may quickly assess for forms of life suitability or capture conditions data over a period of time. Forms of life suitability and recommendations may be presented to a user on a mobile device, in augmented reality, virtual reality, emailed, text messaged, or any other computer-based tool or web interface. A user may be enabled to purchase or sell forms of life or recommendations through an e-commerce platform, digital or virtual marketplace through an app, mobile device, or other platform.

Satellite Method for Forms of Life Suitability. Satellite method for forms of life suitability may include incorporating satellite imagery and other data to make recommendations assessing solar radiation values, forms of life suitability, care, accessories, services, or other potential uses. This may be used to assess conditions of larger areas and support in identifying obstacles, landscape features, or other conditions that could impact recommendations.

Conditions Hardware. Conditions hardware may include the incorporation of one or more types of hardware and software to assess conditions, for a period of time or episodically. These may include hardware designed to quantify conditions data, hardware that supports forms of life care, automation hardware and more. These hardwares may be integrated with computer-based tools and software solutions. They may include Tot devices, such as with moisture sensors, temperature sensors, or chlorophyll meters. Examples may be, an irrigation system to deliver water and nutrients, soil sensors, and many more forms. This could be used to create a continuous assessment system.

As will be realized, the systems and methods disclosed herein are capable of other and different embodiments and its several details may be capable of modifications in various respects, all without departing from the invention as set out in the appended claims. Accordingly, the drawings and description are to be regarded as illustrative in nature and not in a restrictive or limiting sense with the scope of the application being indicated in the claims.

What is claimed is:

1. A method of evaluating one or more forms of life and classifying form of life suitability for a location by assessing one or more solar radiation values in the location for a period of time, the method comprising:

capturing sky exposure data in a location along at least some part of one or more solar paths between a winter solstice solar path and a summer solstice solar path using one or more data collection sensors;

evaluating captured sky exposure data using one or more computer-based tools;

classifying portions of the captured sky exposure data as indicative of at least one of sky and sky blockages;
assessing one or more solar radiation values received by at least some of the location during at least an instant in time, based at least in part on the captured sky exposure data;
evaluating one or more forms of life based at least in part on one or more of the assessed solar radiation values;
and classifying form of life suitability based at least in part on the evaluation of one or more forms of life and also based at least in part on one or more of the assessed solar radiation values.

2. The method of evaluating and classifying forms of life suitable to a location of claim 1, further comprising:
presenting to a user one or more of the solar paths at the location;
and instructing the user to orient one or more data collection sensors to capture additional solar radiation values at the location.

3. The method of evaluating and classifying forms of life suitable to a location of claim 1, further comprising:
estimating insurance-related parameters relating to one or more of the forms of life.

4. The method of evaluating and classifying forms of life suitable to a location of claim 1, further comprising:
incorporating additional data, including at least some conditions data, in the evaluation of one or more forms of life and in the classification of form of life suitability.

5. The method of evaluating and classifying forms of life suitable to a location of claim 1, further comprising:
recommending a customized care plan for at least one of the one or more forms of life based at least in part on one or more of the assessed solar radiation values.

6. The method of evaluating and classifying forms of life suitable to a location of claim 1, further comprising:
mapping data from at least one of the one or more solar radiation values into a model based at least in part on the classification of form of life suitability.

7. The method of claim 6, further comprising:
implementing at least a portion of the model via remote operation.

8. The method of evaluating and classifying forms of life suitable to a location of claim 1, further comprising:
capturing additional sky exposure data along at least some additional part of the one or more solar paths between the winter solstice solar path and the summer solstice solar path, at least in the form of image data;
and assessing additional portions of at east one of the one or more solar paths using the captured additional sky exposure image data, using one or more computer-based systems.

9. The method of evaluating and classifying forms of life suitable to a location of claim 1, further comprising:
improving performance of at least one of evaluating one or more forms of life and classifying form of life suitability by utilizing additional data from disparate locations.

10. The method of evaluating and classifying forms of life suitable to a location of claim 1, further comprising:
presenting to the user one or more recommendations based at least in part on one or more of the evaluation of one or more forms of life, the classification of form of life suitability, and one or more of the solar radiation values.

11. The method of evaluating and classifying forms of life suitable to a location of claim 1, further comprising:
quantifying a productivity value of at least one of the forms of life, based at least in part on one or more of the solar radiation values.

12. The method of evaluating and classifying forms of life suitable to a location of claim 1, further comprising:
providing medium enhancing recommendations to the user based at least in part on the evaluation of one or more forms of life, the classification of form of life suitability, and conditions data.

13. The method of evaluating and classifying forms of life suitable to a location of claim 1, further comprising:
assessing health status of one or more of the forms of life;
and providing one or more health solutions recommendations to the user, based at least in part on the assessed health status of the one or more forms of life.

14. The method of evaluating and classifying forms of life suitable to a location of claim 1, further comprising:
appraising one or more of the forms of life using computer-based systems.

15. The method of evaluating and classifying forms of life suitable to a location of claim 1, further comprising:
providing training recommendations to improve forms of life caring skills.

16. The method of evaluating and classifying forms of life suitable to a location of claim 1, further comprising:
providing one or more structural modification recommendations for the location based at least in part on the evaluation of one or more forms of life and based at least in part on conditions data.

17. The method of evaluating and classifying forms of life suitable to a location of claim 1, further comprising:
enabling at least one of the purchase and sale of at least one of a form of life and a recommendation.

18. The method of evaluating and classifying forms of life suitable to a location of claim 1, further comprising:
assessing human wellness factors related to one or more of the evaluation of forms of life and one or more of the solar radiation values.

19. A system to evaluate one or more forms of life and classify form of life suitability for a location by assessing one or more solar radiation values in the location for a period of time, the system comprising:
one or more data collection sensors for capturing sky exposure data in a location along at least some part of one or more solar paths between a winter solstice solar path and a summer solstice solar path;
one or more computer-based tools for evaluating captured sky exposure data;
control logic for classifying portions of the captured sky exposure data as indicative of at least one of sky and sky blockages;
control logic for assessing one or more solar radiation values received by at least some of the location during at least an instant in time, based at least in part on the captured sky exposure data;
control logic for evaluating one or more forms of life based at least in part on one or more of the assessed solar radiation values;
and control logic for classifying form of life suitability based at least in part on the evaluation of one or more forms of life and also based at least in part on one or more of the assessed solar radiation values.

20. A non-transitory computer readable medium storing instructions that when executed by one or more processors cause the one or more processors to:
capture sky exposure data in a location along at least some part of one or more solar paths between a winter solstice solar path and a summer solstice solar path using one or more data collection sensors;

evaluate captured sky exposure data using one or more computer-based tools;

classify portions of the captured sky exposure data as indicative of at least one of sky and sky blockages;

assess one or more solar radiation values received by at least some of the location during at least an instant in time, based at least in part on the captured sky exposure data;

evaluate one or more forms of life based at least in part on one or more of the assessed solar radiation values;

and classify form of life suitability based at least in part on the evaluation of one or more forms of life and also based at least in part on one or more of the assessed solar radiation values.

* * * * *